(12) United States Patent
Sohn et al.

(10) Patent No.: US 12,297,163 B2
(45) Date of Patent: *May 13, 2025

(54) GLYCEROL DERIVATIVE, PREPARATION METHOD THEREFOR, AND IMMUNOMODULATOR COMPRISING SAME AS EFFECTIVE INGREDIENT

(71) Applicant: ENZYCHEM LIFESCIENCES CORPORATION, Jecheon-si (KR)

(72) Inventors: Ki Young Sohn, Seoul (KR); Jae Wha Kim, Daejeon (KR); Sun Young Yoon, Daejeon (KR); Chang Hyun Yoo, Daejeon (KR); Jin Seon Jeong, Cheonan-si (KR)

(73) Assignee: ENZYCHEM LIFESCIENCES CORPORATION, Jecheon-si (KR)

(*) Notice: Subject to any disclaimer, the term of this patent is extended or adjusted under 35 U.S.C. 154(b) by 755 days.

This patent is subject to a terminal disclaimer.

(21) Appl. No.: 17/047,123

(22) PCT Filed: Apr. 19, 2019

(86) PCT No.: PCT/KR2019/004789
§ 371 (c)(1),
(2) Date: Oct. 13, 2020

(87) PCT Pub. No.: WO2019/208980
PCT Pub. Date: Oct. 31, 2019

(65) Prior Publication Data
US 2021/0198183 A1 Jul. 1, 2021

(30) Foreign Application Priority Data
Apr. 23, 2018 (KR) .................. 10-2018-0046890

(51) Int. Cl.
| | |
|---|---|
| *C07C 233/20* | (2006.01) |
| *A23L 33/12* | (2016.01) |
| *A61K 31/133* | (2006.01) |
| *A61K 31/231* | (2006.01) |
| *A61P 29/00* | (2006.01) |
| *A61P 31/04* | (2006.01) |
| *A61P 31/12* | (2006.01) |
| *A61P 35/00* | (2006.01) |
| *A61P 37/06* | (2006.01) |
| *A61P 37/08* | (2006.01) |
| *C07C 69/708* | (2006.01) |
| *C07C 69/73* | (2006.01) |
| *C07C 233/18* | (2006.01) |
| *C07C 233/38* | (2006.01) |
| *C07C 235/06* | (2006.01) |
| *C07C 235/28* | (2006.01) |
| *C07C 327/28* | (2006.01) |

(52) U.S. Cl.
CPC .......... *C07C 233/20* (2013.01); *A61P 37/06* (2018.01); *C07C 69/708* (2013.01); *C07C 233/18* (2013.01); *C07C 233/38* (2013.01); *C07C 235/06* (2013.01); *C07C 327/28* (2013.01)

(58) Field of Classification Search
CPC ... C07C 233/20; C07C 69/708; C07C 233/18; C07C 233/38; C07C 235/06; C07C 327/28; C07C 69/73; C07C 2601/02; C07C 2601/14; C07C 235/28; A61P 37/06; A61P 31/04; A61P 37/08; A61P 29/00; A61P 31/12; A61P 35/00; A23L 33/12; A61K 31/231; A61K 31/133
See application file for complete search history.

(56) References Cited

U.S. PATENT DOCUMENTS

| | | | |
|---|---|---|---|
| 4,221,732 A | 9/1980 | Oette et al. | |
| 5,059,442 A * | 10/1991 | Klemann | A23D 7/0056 426/531 |
| 2018/0264105 A1 | 9/2018 | Kugimiya et al. | |

FOREIGN PATENT DOCUMENTS

| | | | |
|---|---|---|---|
| DE | 277700 | * 6/1988 | |
| GB | 2020663 | 11/1979 | |
| GB | 2021579 | 12/1979 | |
| JP | 1979-148727 | 11/1979 | |
| KR | 10-2006-0047447 | 5/2006 | |
| KR | 20110088991 | 8/2011 | |
| WO | 2004/090096 | 10/2004 | |
| WO | 2005/112912 | 12/2005 | |
| WO | WO-2005112912 A1 * | 12/2005 | ............... A21D 2/16 |
| WO | 2008/075983 | 6/2008 | |
| WO | 2008/113177 | 9/2008 | |

(Continued)

OTHER PUBLICATIONS

Merriam-Webster. "Immunomodulator." Merriam-Webster.com Dictionary, Merriam-Webster, https://www.merriam-webster.com/dictionary/immunomodulator. Accessed Mar. 23, 2023. See Appendix for year. (Year: 2023).*

(Continued)

*Primary Examiner* — Susanna Moore
*Assistant Examiner* — Luisalberto Gonzalez
(74) *Attorney, Agent, or Firm* — LEX IP MEISTER, PLLC

(57) ABSTRACT

Disclosed are a glycerol derivative that is useful for improving, preventing or treating inflammation-related diseases by inhibiting overexpression of various inflammatory cytokines such as IL-4, IL-6 and so on, or chemokine CXCL8 and reducing migration of HL-60 cell lines, preparation method therefor, and an immunomodulator containing the same as active ingredient. It includes a glycerol derivative represented by Chemical formula 2 or 3 in the specification.

2 Claims, 6 Drawing Sheets

(56) References Cited

FOREIGN PATENT DOCUMENTS

| WO | 2009/060457 | | 5/2009 | |
| WO | WO-2009060457 A1 | * | 5/2009 | ........... A61K 31/133 |
| WO | 2017/057540 | | 4/2017 | |

OTHER PUBLICATIONS

Mortensen, EFSA Journal 2017; 15( 5):4785, 48 pp (Year: 2017).*
Yoon et al (Immune Network, 2015; 15(2): 100-109 (Year: 2015).*
Ward, Chemistry and Physics of Lipids, 47 (1988) 217-224. (Year: 1988).*
Schick et al, Journal fuer Praktische ChemiChemiker Zeitung, 1993, 335(7), 628-632 (Year: 1993).*
Schick, J. prakt. Chem. 335 (1993) 628-632 (Year: 1993).*
EPO, search report of EP 19792728.8 dated Feb. 25, 2022.
Hung the Dang et al., "Evaluation of endogenous fatty acid amides and their synthetic analogues as potential anti-inflammatory leads", Bioorganic & Medicinal Chemistry, vol. 19 (2011) 1520-1527.
J.P. Ward, "Synthesis of hydroxy thiol esters from glycidol esters", Chemistry and Physics of Lipids, vol. 47 (1988), 217-224.
Soheila Bahmanjah et al., "Monoacylglycerols as transmembrane c1-anion transporters", Chemical Communications, vol. 48, No. 37 (2012), 4432-4434.
STN Chemical compound, RN 2188187-26-8 (Mar. 9, 2018).
STN Chemical compound, RN 1482022-29-6 (Nov. 27, 2013).
STN Chemical compound, RN 1027540-85-7 (Jun. 12, 2008).
STN Chemical compound, RN 1026587-59-6 (Jun. 8, 2008).
Lucie Couturier et al., "Lipase-catalyzed chemoselective aminolysis of various aminoalcohols with fatty acids", Journal of Molecular Catalysis B Enzymatic, vol. 56, No. 1, pp. 29-33, Jan. 2009.
KIPO, International Search Report of PCT/KR2019/004789, dated Aug. 14, 2019.
KIPO, Written Opinion International Preliminary Report of PCT/KR2019/004789, Oct. 27, 2020.
Arantxa Rodriguez et al., "Palladium-Catalyzed Three-Component Coupling Reactions: 1,1-Difunctionalization of Activated Alkenes", Eur. J. Org. Chem., 2009: 1313-1316. https://doi.org/10.1002/ejoc.200801245.
H. Schick et al., "Synthesis of Alkyl (.+--.)-2,3,-Di-O-acylglycerates and Attempts Directed to their Conversion into Alkyl (R)-2-,3-Di-O-acylglycerates by Enzyme-catalyzed Enantioselective Deacylation Reactions", Journal fuer Praktische ChemieChemiker Zeitung 1993, 335(7), 628-632.
The description of Tosko German Patent No. 277700.
The description of Tosko German Patent No. 277699.
Haipeng Liu et al., "Membrane Anchored Immunostimulatory Oligonucleotides for In Vivo Cell Modification and Localized Immunotherapy", Angewandte Chemie, International Edition (2011), 50(31), 7052-7055.
Farooqui, A.A. et al., "Purification characterization and cDNA cloning of bovine brain diacylglycerol lipase", Biochemical Society Transactions (1988), 16(3), 293.
JPO, Office Action of JP 2020558931 dated Nov. 24, 2021.

* cited by examiner

GLYCEROL DERIVATIVE, PREPARATION METHOD THEREFOR, AND IMMUNOMODULATOR COMPRISING SAME AS EFFECTIVE INGREDIENT

TECHNICAL FIELD

The present invention relates to a glycerol derivative, a preparation method therefor, and an immunomodulator comprising same as effective ingredient, more particularly, to a glycerol derivative which inhibits overexpression of various inflammatory cytokines such as IL-4, IL-6 and so on, and CXCL8, and thereby is useful for improving, preventing or treating inflammation-related diseases, a preparation method therefor, and an immunomodulator containing the same as active ingredient.

BACKGROUND ART

Immunity is a defense mechanism of a living body against various pathogens, and immunodeficiency is an occurrence of defects in some components of the immune system. As a result, immune response does not occur for many types of antigens, and these immune deficiencies are largely divided into a congenital or primary immunodeficiency and an acquired or secondary immunodeficiency. The congenital immunodeficiency can only be treated by gene therapy, antibody injection, or bone marrow transplantation, as immune cells such as B cells and T cells do not exist originally. On the other hand, in the acquired immunodeficiency syndrome, the immune component itself originally exists, but an abnormality occurs in the immune response process exhibited by them. Therefore, the immunodeficiency status can be improved by enhancing the function of immune components. Also, in recent years, there are many autoimmune diseases such as arthritis, atopy, dementia, and sepsis, that occur due to an abnormal increase in immune function. In this case, although immunosuppressants are mainly used for treatment, but they deteriorate overall immunity in many cases and cause other problems. Recently, as the action mechanism of immune function is known, attempts are being made to develop immunomodulatory substances that can enhance or suppress immune function. Such an attempt is to regulate, specifically to enhance or to suppress the immune function of the living body by stimulating immune cells non-specifically through an immunomodulatory substance, thereby enhancing the body's defense mechanism against disease factors and minimizing side effects at the same time. As such an immunomodulatory substance, Korean Patent Laid Open No. 10-2006-0047447 discloses a monoacetyldiacyl glycerol compound of the following Chemical formula 1. The compound of Formula 1 is 1-palmitoyl-2-linoleoyl-3-acetylglycerol, and is commonly known as EC-18 or PLAG.

[Chemical formula 1]

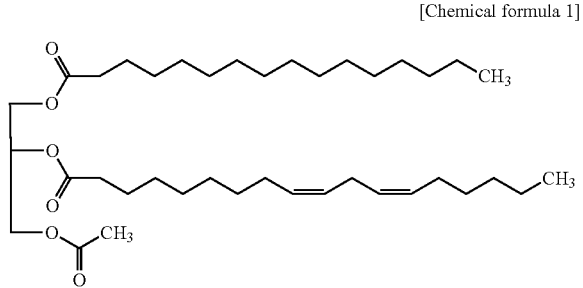 [SMILES: CCCCC/C=C\C/C=C\CCCCCCCC(=O)OC(COC(C)=O)COC(=O)CCCCCCCCCCCCCCC]

The compound of Chemical formula 1 is known to have efficacy in the inhibition, prevention, and treatment of diseases caused by a decrease in various immune functions and cell damage caused by autoimmune function, for example cancer, sepsis, arthritis, infection, dementia, aging, diabetes, skin disease, asthma, atopy, stress, nervous breakdown, chronic fatigue syndrome and so on.

DISCLOSURE OF INVENTION

Therefore, an object of the present invention is to provide a glycerol derivative having an immunomodulatory function similar to 1-palmitoyl-2-linoleoyl-3-acetylglycerol (EC-18), a conventional immunomodulatory substance, preparation method therefor, and immunomodulator containing same as active ingredient.

Another object of the present invention is to provide a glycerol derivative for improving, preventing or treating inflammation-related diseases by inhibiting overexpression of inflammatory cytokines such as IL-4, IL-6 and so on, or chemokine CXCL8 involved in a migration of inflammatory cells, preparation method therefor, and immunomodulator containing same as active ingredient.

In some embodiments for achieving the above objects, the present invention provides a glycerol derivative represented by the following Chemical formula 2 or 3.

[Chemical formula 2]

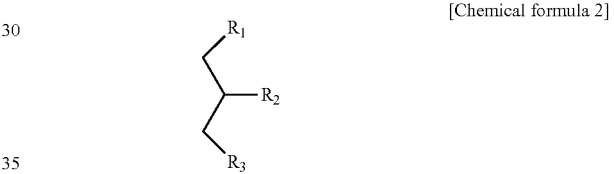

In Chemical formula 2, at least one of $R_1$, $R_2$ and $R_3$ is —$NHR_4$ or —$SR_4$ (herein, $R_4$ is a chain-type fatty acid group having 2 to 18 carbon atoms.), and the remainder is —OC(=O)$R_5$ (herein, $R_5$ is a chain or branched aliphatic hydrocarbon group having 1 to 17 carbon atoms or a cyclic aliphatic hydrocarbon group having 3 to 6 carbon atoms) or —OH.

[Chemical formula 3]

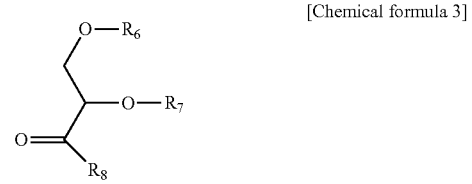

In Chemical formula 3, $R_6$ and $R_7$ are independently a fatty acid group having 2 to 18 carbon atoms, and $R_8$ is —$OR_9$ or —$NHR_9$ (herein, $R_9$ is alkyl group having 1 to 3 carbon atoms).

In addition, the present invention provides an immunomodulator comprising the glycerol derivative represented by Chemical formula 2 or 3 as an active ingredient.

In addition, the present invention provides a health functional food composition for modulating immunity comprising the glycerol derivative represented by Chemical formula 2 or 3 as an active ingredient.

According to the glycerol derivative, preparation method therefor, and immunomodulator containing same as active ingredient of the present invention, it is provided a compound useful for improving, preventing or treating inflammation-related diseases by inhibiting overexpression of inflammatory cytokines such as IL-4 and IL-6, or chemokine CXCL8 involved in the migration of inflammatory cells.

BEST MODES FOR CARRYING OUT THE INVENTION

Figure 1:
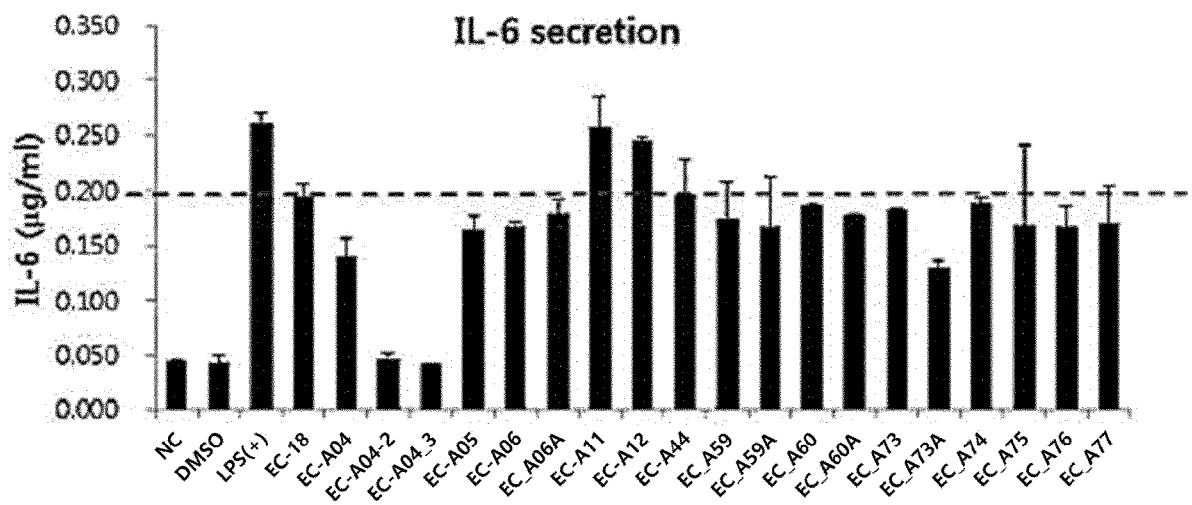
FIGS. 1 and 2 are graphs showing the degree of IL-6 secretion induced by LPS according to an embodiment of the present invention.

Hereinafter, the present invention will be described in detail.

The present invention provides a novel glycerol derivative represented by the following Chemical formula 2 or 3. Specifically, a novel glycerol derivative represented by the following Chemical formula 2, and a novel glycerol derivative in which a carbonyl group is introduced into a backbone represented by the following Chemical formula 3 are provided.

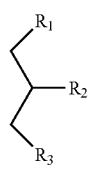

[Chemical formula 2]

In Chemical formula 2, at least one of $R_1$, $R_2$ and $R_3$ is —$NHR_4$ or —$SR_4$ (herein, $R_4$ is a chain-type fatty acid group having 2 to 18 carbon atoms.), and the remainder is —OC(=O)$R_5$ (herein, $R_5$ is a chain or branched aliphatic hydrocarbon group having 1 to 17 carbon atoms or a cyclic aliphatic hydrocarbon group having 3 to 6 carbon atoms) or —OH.

Specifically, the fatty acid group in Ra refers to an acyl group from which a hydroxy group (—OH) has been removed from a chain or branched and saturated or unsaturated fatty acid. For example, it may be acetyl, palmitoyl, linoleoyl, myristoyl, and so on. The aliphatic hydrocarbon group in $R_5$ includes chain, branched or cyclic and saturated or unsaturated hydrocarbons, excluding aromatics. For example, it may be ethyl, propyl, butyl, pentadexyl, heptadecyl-8,11-diene, 1-methylpropyl, tert-butyl, cyclopropyl, cyclohexyl, and so on.

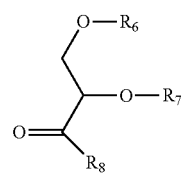

[Chemical formula 3]

In Chemical formula 3, $R_6$ and $R_7$ are each independently a fatty acid group having 2 to 18 carbon atoms, and $R_8$ is —$OR_9$ or —$NHR_9$, and the $R_9$ is alkyl group having 1 to 3 carbon atoms. Specifically, the $R_6$ and $R_7$ may each independently be palmitoyl, linoleoyl, etc., and the $R_9$ may be ethyl, etc.

The glycerol derivative represented by Chemical formula 2 or 3 can be prepared by various methods, for example, the glycerol derivative represented by Chemical formula 2 can be prepared using serinol (2-Amino-1,3-propanediol, $C_3H_9NO_2$, molecular weight: 91.11) as a starting material. The synthesis method using serinol as the starting material, can be typically performed according to the following Reaction 1 to 2.

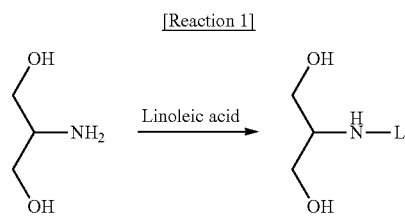

[Reaction 1]

First, as shown in Reaction 1, serinol and linoleic acid (fatty acid) are reacted to obtain glycerol derivative represented by Chemical formula 2.

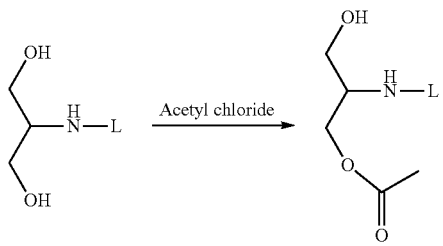

[Reaction 2]

By reacting acetyl chloride with the compound synthesized in the Reaction 2, the glycerol derivative represented by Formula 2 may be obtained.

The glycerol derivative of the present invention, similar to the monoacetyldiacylglycerol derivative (EC-18) represented by Formula 1, which shows an effect in various acute and chronic inflammatory diseases as a conventional immunomodulator and anticancer agent, can regulate the expression of inflammatory cytokines in macrophages that initially respond to human infection, and can be used as an immunomodulator. Specifically, the 1,2-diacylglycerol compound of the present invention can inhibit overexpression of IL-6, an inflammatory cytokine, and reduce STAT3 activity, an IL-6 expression regulate factor. Therefore, it can be used as an improvement, prevention and therapeutic agent of various acute and chronic inflammatory diseases and diseases related to immune diseases. In addition, as a conventional immunomodulatory and anticancer agent, similar to the monoacetyldiacylglycerol derivative (EC-18) represented by the Chemical formula 1, which exhibits an effect in various acute and chronic inflammatory diseases, it can be used as an immunomodulator by regulating the expression of inflammatory cytokines in macrophages initially responding to human infection. Specifically, the glycerol derivative of the present invention regulates and reduces the expression of IL-4 expressed in T hepler 2 type (Th2) T cells, which affects the microenvironment of various allergic and autoimmune diseases, and further cancer. Also, since it has the effect of reducing the STAT6 activity, the expression regulate factor of these cytokines, it can be used as a preventive and therapeutic agent for Th2-related chronic diseases and cancer. In addition, it has the effect of inhibiting the expression of IL-6, an inflammatory cytokine in RAW 265.7 cells, one of the macrophage cell lines, and has the effect of reducing the activity of STAT3, an IL-6 expression regulator. As an agent for improving various inflammatory diseases, it is not toxic and can be usefully used as a preventive and therapeutic agent for various grade, chronic inflammatory diseases and diseases related to immune diseases.

Similar to conventional glycerol derivatives, it is effective to control and reduce the expression of CXCL8 in THP-1 cells, and eventually reduce excessive neutrophil migration, thereby inhibiting infection in an acute bronchial infection model in an animal model. Therefore, as an immunomodulator that modulates the inflammatory response due to excessive neutrophil migration, it is a therapeutic agent that responds to initial infection and is not toxic and can be usefully used as a preventive and therapeutic agent for various grade, chronic inflammatory diseases and diseases related to immune diseases.

In addition, by using a Transwell, the migration of the HL-60 cell line, which is an undifferentiated neutrophil cell line, is reduced, and can be usefully used as a prevention and therapeutic agent for cancer-related diseases by inhibiting metastasis and changing the cancer microenvironment.

Examples of immune-related diseases that can be prevented or treated by the administration of the glycerol derivative of the present invention may include various bacterial and viral infection diseases, acute and chronic inflammatory lung diseases, pneumonia, autoimmune disease, allergic disease, cancer, and so on. As used herein, the term "prevention" or "preventing" includes any activity to suppress the overexpression of immunity by administering the derivative of the present invention. The term "treatment" or "treating" includes any activity to improve or beneficially alter the symptoms of immune-related diseases by the derivative of the present invention.

The glycerol derivative of present invention may be used as an immunomodulator alone without mixing other substance, or in the form of a pharmaceutical composition containing the glycerol derivative as an active ingredient. When glycerol derivative of present invention is used in the pharmaceutical composition, conventional pharmaceutically acceptable carriers, excipients, or diluents can be included therein. The amount of glycerol derivative in the pharmaceutical composition can be widely varied without specific limitation, and is specifically 0.0001 to 100.0 weight %, specifically, 0.001 to 95.0 weight %. For example, the amount of the glycerol derivative in the composition may be included in an amount of 0.01 to 50% by weight, more specifically 1 to 20% by weight. Also, the amount of the glycerol derivative in the composition may be included in an amount of 50 to 100% by weight, more specifically 50 to 95% by weight.

The pharmaceutical composition may be formulated into any one selected from the group consisting of tablets, bolus, powders, granules, capsules, suspensions, liquid solutions, emulsions, syrups, sterilized aqueous solutions, non-aqueous solutions, suspensions, emulsions, freeze-dried agents, and suppositories and so on, and may be formulated into various forms for oral or non-oral administration. In formulating the composition, conventional excipients, or diluents such as fillers, bulking agents, binders, wetting agents, disintegrating agents, and surfactants can be used. The solid formulation for oral administration includes tablet, bolus, powder, granule, capsule and so on, and such solid formulations can be prepared by mixing one or more of the components and at least one excipient such as starch, calcium carbonate, sucrose, lactose, gelatin, and so on. Besides the excipient, a lubricant such as Magnesium stearate and talc can also be used. The liquid formulation for oral administration includes suspension, liquid solutions, emulsion, syrup, and so on, and may include conventional diluents such as water and liquid paraffin or may include various excipients such as wetting agents, sweeting agents, flavoring agents, and preserving agents. The formulation for non-oral administration includes sterilized aqueous solution, non-aqueous solution, suspension, emulsion, freeze-dried formulation, suppository, and so on, and solvent for solution such as non-aqueous solution, suspension may include propylene glycol, polyethylene glycol, vegetable oils such as olive oil, and ester for syringe injection such as ethyl oleate. Base materials of the suppository may include witepsol, macrogol, tween 61, cacao butter, Laurin and glycerogelatin.

The composition of present invention can be administered in a pharmaceutically effective amount. The term "pharmaceutically effective amount" is used to refer to an amount that is sufficient to treat a disease at a reasonable benefit/risk ratio applicable to achieve a desired result in a medical treatment. The "pharmaceutically effective amount" can be determined according to the subject's category, age, sex, severity and type of disease, activity of drug, sensitivity to drug, administration time, administration route, excretion rate, duration of treatment, factors including concurrent drugs, and other factors well known in the medical field. The composition of the present invention can be administered alone or with other therapeutic agents sequentially or simultaneously. The composition of the present invention can be administered once or multiple times. It is important to administer an amount capable of obtaining the maximum effect in a minimum amount without side effects in consideration of all of the above factors, which can be easily determined by a person skilled in the art. The preferable amount of the composition of the present invention can be varied according to the condition and weight of patient, severity of disease, formulation type of drug, administration route and period of treatment. An appropriate total amount of administration per 1 day can be determined by a physician, and is generally about 0.001 to about 1000 mg/kg, preferably about 0.05 to 200 mg/kg, more preferable about 0.1 to about 100 mg/kg once a day or can be administered in divided doses multiple times daily. The compound or composition can be applied to any subject without specific limitation as long as it is an individual for the purpose of preventing immunity reduction, of enhancing immunity, or of treating an immune disease. For example, the composition of the present invention can be administered to not only human but also non-human animal (specifically mammals)

such as monkey, dog, cat, rabbit, guinea pig, rat, mouse, cow, sheep, pig, goat, and birds and fishes, and so on. The composition of the present invention can be administered by conventional various methods, for example, by oral or rectum administration, or by intravenous (i.v.), intramuscular (i.m.), subcutaneous (s.c.), intrauterine dural or cerebrovascular injection.

In some embodiments, the present invention provides health functional food compositions for regulating immunity, which comprises a 1,2-diacylglycerol compound represented by Formula 1 above as an active ingredient. Specifically, the glycerol derivative of the present invention may be included in a health functional food composition for preventing immunity overexpression, enhancing immunity, preventing or improving immune-related diseases. The term "improvement" or "improving" refers to any activity to improve or ameliorate the symptoms of an individual who is suspicious of an immune-related disease or developing an immune-related disease.

The health functional food composition may consist of only or substantially pure compound of the present invention or may include compound of the present invention together with other conventional ingredients of health functional food. The amount of the active ingredient in the health food composition can be determined suitably according to the intended use. Generally, when the compound of the present invention is included in food or beverages, the amount of the composition according to the present invention is preferably less than 15 weight %, more preferably less than 10 weight %, with respect to the total amount of the raw material. In case of a long term use for the purpose of the health control and hygiene, the amount can be less than the above range. Since there is no problem in terms of safety, amount of the active component is greater than the above range.

Foods to which the compound of the present invention can be added are not limited, and include various foods, for example, meats, sausages, breads, chocolates, candies, snacks, pizzas, noodles, gums, daily products such as ice creams, soups, beverages, teas, drinks, alcoholic beverages, vitamin complexes and any health functional food, and also include food used as feed for animals. When the health functional food composition of present invention is used in the beverage product, the beverage product may include sweeting agents, flavoring agents or natural carbohydrates. Examples of natural carbohydrates include monosaccharides such as glucose and fructose, disaccharides such as maltose and sucrose, polysaccharides such as dextrin and cyclodextrin, and sugar alcohols such as xylitol, sorbitol and erythritol. The amount of carbohydrate in the beverage composition can be widely varied without specific limitation, and is preferably 0.01 to 0.04 g, more preferably, 0.02 to 0.03 g per 100 ml of the beverage. Examples of sweeting agents include natural sweeteners such as thaumatin and *stevia* extract and artificial sweeteners such as saccharin and aspartame. In addition to the above, the health functional food composition of the present invention may include various nutrients, vitamins, electrolytes, flavoring agents, colorants, pectic acid and salts thereof, alginic acid and salts thereof, organic acids, protective colloidal thickening agents, pH controlling agents, stabilizing agents, preserving agents, glycerin, alcohol, carbonizing agents used in carbonated beverages and so on. Moreover, the health functional food composition of the present invention may include fruits, as used in preparing natural fruit juices and fruit juice beverages and vegetable beverages.

In some embodiments, the present disclosure provides methods for regulating immunity or preventing or treating an immune overexpression or immune-related disease, comprising administering the pharmaceutical composition to a patient in need thereof. The term "a patient in need" includes any animal including human that suffers from immune-related disease or can develop immune-related disease. Immune overexpression or immune-related disease can be treated or prevented by administering an effective amount of a pharmaceutical composition containing a compound of the present invention or containing the compound of the present invention and pharmaceutically acceptable salt thereof to a patient in need thereof. The term "administration" means introducing the pharmaceutical composition of the present invention to a patient in need by any suitable method. The composition of the present disclosure can be administered by conventional various methods, for example, by oral or non-oral administration as far as the target organization can be reached. In some embodiments, the method of the present disclosure comprises administering a therapeutically effective amount of a pharmaceutical composition comprising 1,2-diacylglycerol compound of chemical formula 1 to a patient in need thereof. An appropriate total amount of administration per 1 day can be determined by a physician and is generally about 0.001 to about 1000 mg/kg, preferably, about 0.05 to 200 mg/kg, more preferably about 0.1 to about 100 mg/kg. The total administration amount per day can be administered once a day or can be administered in divided doses multiple times daily. However, the specific therapeutically effective amount of pharmaceutical composition administered to a particular patient can be varied depending on the type and degree of the response to be achieved in the treatment, the specific composition, including whether another agent is included in the composition, the patient's age, body weight, general health status, sex, diet, administration time, administration route, the ratio of composition, treatment period, other drugs used together in the treatment and a variety of factors well known in the medical field.

EMBODIMENTS FOR CARRYING OUT THE INVENTION

Hereinafter, the present invention is described in more detail through examples. The following example is only to help the understanding of the present invention, and the present invention is not limited by the following examples.

[Example 1] Synthesis of Glycerol Derivative (EC-A04_2)

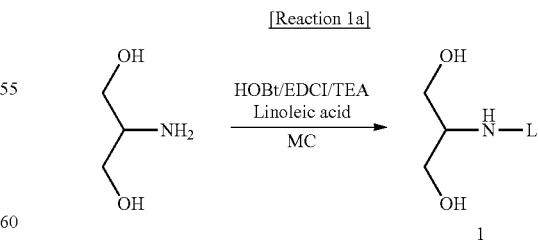

2-Amino propane-1,3-diol (1.5 eq.) as starting material, Triethylamine (TEA, 6 eq.), linoleic acid (2 g, 7.13 mmole, 1 eq.), HOBt (1-Hydroxybenzotriazole, 1.2 eq.) and EDCI (N-(3-Dimethylamino propyl)-N'-ethylcarbodiimide, 1.2 eq.) were added to 500 ml of MC(Methylene chloride), and stirred at 25° C. for 18 hours. The solvent was concentrated and purified by column (MC:MeOH=100:1→10:1) to obtain the target compound 1 (L=linoleoyl, MeOH=methanol, yield 90.46%).

[Example 2] Synthesis of Glycerol Derivative (EC-A04_3)

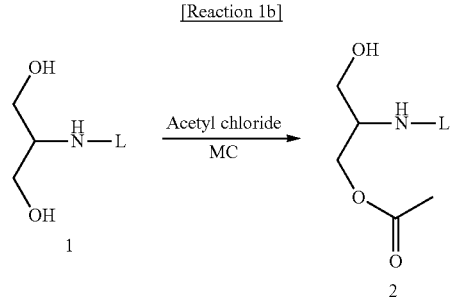

Compound 1 synthesized in Example 1 (EC-A04_2, 1 g, 2.83 mmole, 1 eq.) was added and dissolved to 10 ml of MC(Methylene chloride). And acetyl chloride (0.8 eq.) was slowly added dropwise while maintaining 0° C. The reaction solution was stirred at 25° C. for 18 hours. The solvent was concentrated and purified by column (MC:MeOH=10:1→1:1) to obtain the target compound 2 (yield 74.25%).

[Example 3] Synthesis of Glycerol Derivative (EC-A04)

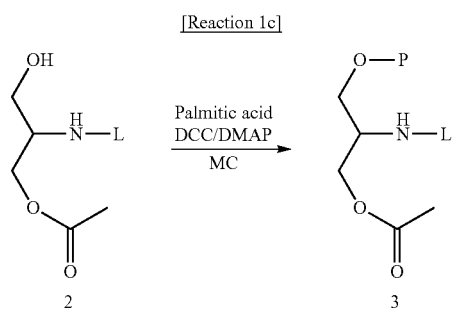

Compound 2 synthesized in Example 2 (EC-A04_3, 100 mg, 252.8 mmole, 1 eq.), DCC (N,N'-Dicyclohexylcarbodiimide, 1.2 eq.) and DMAP (4-(Dimethylamino)pyridine, 0.2 eq.) were added to 100 ml of MC(Methylene chloride), and stirred at 25° C. for 18 hours. The solvent was concentrated and purified by column (PE (Petroleum ether):EA (Ethyl acetate)=30:1→10:1) to obtain the target compound 3 (P=palmitoyl, L=linoleoyl, yield 60.4%).

[Example 4] Synthesis of Glycerol Derivative (EC-A06)

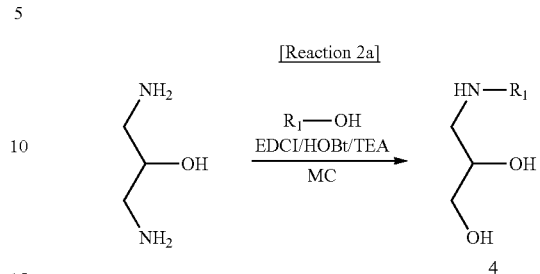

3-Amino-1,2-propane diol (1.2 eq.) as starting material, $R_1$—OH (1 g, 3.9 mmol, 1 eq.), EDCI (N-(3-Dimethylamino propyl)-N'-dethylcarbodiimide, 1.2 eq.), HOBt (1-Hydroxybenzotriazole, 1.2 eq.) and TEA (6 eq.) were added to 360 ml of MC(Methylene chloride), and stirred at 20° C. for 16 hours. The reaction was confirmed by TLC (MC:MeOH=10:1) (TLC=Thin Layer Chromatography). SM was completely consumed. The solvent was concentrated and purified by column (MC:MeOH=20:1→10:1) to obtain the target compound 4 ($R_1$=palmitoyl, yield 53.22%).

[Reaction 2b]

Compound 4 synthesized in Reaction 2a (720 mg, 2.18 mmole, 1 eq.) was added to 10 ml of THF (Tetrahydrofuran), and TBDPSCI (tert-Butyldiphenylchlorosilane, 1.2 eq.) and imidazole (2 eq.) were added, and stirred at 20° C. for 16 hours. The reaction was confirmed by TLC (MC:MeOH=10:1, Rf=0.7). SM was completely consumed. The reaction solution was concentrated and purified by column to obtain the target compound 5 (R1=palmitoyl, TBDPS=tert-butyldiphenylsilyl, yield=76.73%).

[Reaction 2c]

Compound 5 synthesized in Reaction 2b (500 mg, 880.41 mmole, 1 eq.), R₂—OH (1.05 eq.), DCC (1.05 eq.) and DMAP (0.1 eq.) were added to 1 ml of MC, and stirred at 20~25° C. for 16 hours. The reaction was confirmed by TLC (PE:EA=3:1, Rf=0.35). SM was completely consumed. The reaction solution was concentrated and purified by column (PE:EA=3:1→1:1) to obtain the target compound 6 (R₁=palmitoyl, R2=linoleoyl, yield=64.98%).

[Reaction 2d]

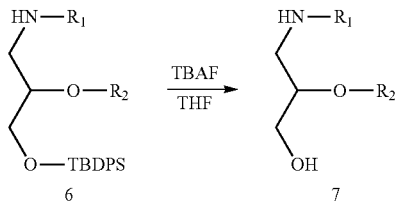

Compound 6 synthesized in Reaction 2c (500 mg, 602.16 mmole, 1 eq.) and TBAF (Tetrabutylammonium fluoride hydrate, 1.5 eq.) were added to 6 ml of THF and stirred at 20~25° C. for 16 hours. The reaction was confirmed by TLC (PE:EA=3:1, Rf=0.1). SM was completely consumed. The reaction solution was concentrated and purified by column (PE:EA=3:1→1:1) to obtain the target compound 7 (R₁=palmitoyl, R2=linoleoyl, yield=90.34%).

[Reaction 2e]

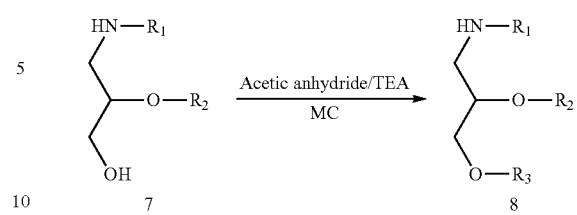

Compound 7 synthesized in Reaction 2d (500 mg, 602.16 mmole, 1 eq.), acetic anhydride (1.2 eq.) and TEA (2 eq.) were added to 1 ml of MC and stirred at 20~25° C. for 16 hours. The reaction was confirmed by TLC (PE:EA=3:1, Rf=0.35). SM was completely consumed. The reaction solution was concentrated and purified by column (PE:EA=3:1) to obtain the target compound 8 (EC_A06, R₁=palmitoyl, R₂=linoleoyl, R₃=acetyl, yield=19.47%).

[Example 5 to 21] Synthesis of Glycerol Derivative

In substantially the same manner as in Example 4, the glycerol derivative compounds shown in Table 1 below were synthesized. And it is shown in Table 1 below along with the yield of the final synthesis step.

TABLE 1

| Example | Compound | R1 group | R2 group | R3 group | Yield(%) |
|---|---|---|---|---|---|
| 5 | EC-A06A | Palmitoyl | Acetyl | Linoleoyl | 22.17 |
| 6 | EC-A11 | Acetyl | Linoleoyl | Palmitoyl | 46.33 |
| 7 | EC-A73 | Palmitoyl | Linoleoyl | 2-Methylbutyryl | 37.3 |
| 8 | EC-A73A | Palmitoyl | 2-Methylbutyryl | Linoleoyl | 29.8 |
| 9 | EC-A74 | Myristoyl | Linoleoyl | Acetyl | 42.7 |
| 10 | EC-A75 | Palmitoyl | Linoleoyl | Propionyl | 53.0 |
| 11 | EC-A76 | Palmitoyl | Linoleoyl | Butyryl | 63.9 |
| 12 | EC-A77 | Palmitoyl | Linoleoyl | Cyclopropanecarbonyl | 44.9 |
| 13 | EC-A81 | Palmitoyl | Linoleoyl | Cyclohexanecarbonyl | 38.7 |
| 14 | EC-A104 | Myristoyl | Acetyl | Linoleoyl | 50.1 |
| 15 | EC-A105 | Myristoyl | Cyclopropanecarbonyl | Linoleoyl | 37.7 |
| 16 | EC-A106 | Myristoyl | 2-Methylbutyryl | Linoleoyl | 48.9 |
| 17 | EC-A107 | Myristoyl | Pivaloyl | Linoleoyl | 50.7 |
| 18 | EC-A111 | Palmitoyl | Propionyl | Linoleoyl | 59.7 |
| 19 | EC-A112 | Palmitoyl | Butyryl | Linoleoyl | 60.3 |
| 20 | EC-A113 | Palmitoyl | Cyclopropanecarbonyl | Linoleoyl | 27.1 |
| 21 | EC-A114 | Palmitoyl | Cyclohexanecarbonyl | Linoleoyl | 31.7 |

[Example 22] Synthesis of Glycerol Derivative (EC-A44)

[Reaction 3a]

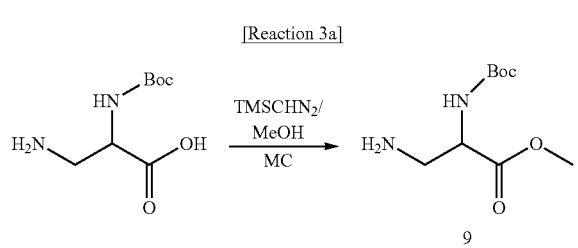

2-[(tert-Butoxycarbonyl)amino]-3-aminopropionic acid (Boc-Dap-OH, 10 g, 48.97 mole, 1 eq.) as starting material, and MeOH (16 ml) were added to 160 ml of MC, and (Trimethylsilyl)diazomethane (TMSCHN$_2$, (Trimethylsilyl)diazomethane solution, 2.0 M in Hex. or diethyl ether, 1.07 eq.) was slowly added dropwise, and stirred at 20~25° C. for 16 hours. The reaction was confirmed by TLC (MC:MeOH=10:1, Rf=0.5). SM was completely consumed. The reaction solution was filtered to obtain the target compound 9.

[Reaction 3b]

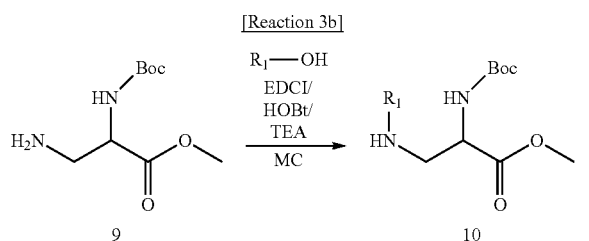

Compound 9 synthesized in Reaction 3a (1.2 eq.), R$_1$—OH (9.5 g, 37.05 mmole, 1 eq.), EDCI (1.2 eq.), HOBt (1.2 eq.) and TEA (6 eq.) were added to 100 ml of MC in the N$_2$-purge, and stirred at 20~25° C. for 16 hours. The reaction was confirmed by TLC (PE:EA=2:1, Rf=0.5). SM was completely consumed. The reaction solution was concentrated and purified by column (PE:EA=5:1→3:1) to obtain the target compound 10 (R$_1$=palmitoyl, yield=32%).

[Reaction 3c]

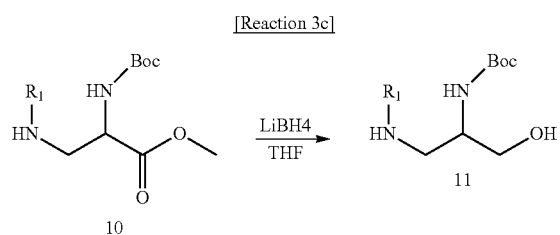

Compound 10 synthesized in Reaction 3c (2.1 g, 4.6 mmole, 1 eq.) was added to 20 ml of THF, and LiBH$_4$ (4 eq.) was added at 0° C. and stirred at 0~20° C. for 1 hour. The reaction was confirmed by TLC (PE:EA=2:1, Rf=0.15). SM was completely consumed. Purified water and ethyl acetate (EA) were added to the reaction solution and extracted three times. The organic layer was washed back with brine solution (Brine soln.), dehydrated with sodium sulfate (Na$_2$SO$_4$), filtered, and concentrated to obtain the target compound 11 (R$_1$=palmitoyl, yield=91.54%).

[Reaction 3d]

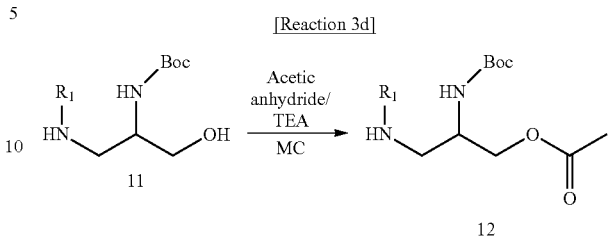

Compound 11 synthesized in Reaction 3c (200 mg, 466.58 mmole, 1 eq.) was added to 2 ml of MC. And after adding acetic anhydride (1.2 eq.) and TEA (2 eq.) at 0° C., the mixture was stirred at 0~20° C. for 16 hours. The reaction was confirmed by TLC (PE:EA=2:1, Rf=0.4). SM was completely consumed. Purified water and MC were added to the reaction solution and extracted three times. The organic layer was washed back with brine solution (Brine soln.), dehydrated with sodium sulfate (Na$_2$SO$_4$), filtered, and concentrated to obtain the target compound 12 (R$_1$=palmitoyl, yield=86.06%).

[Reaction 3e]

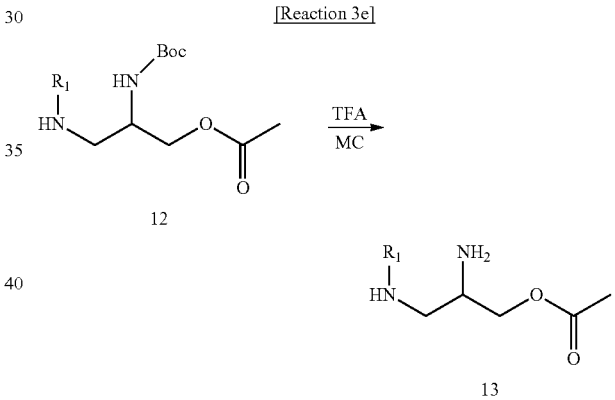

Compound 12 synthesized in Reaction 3d (230 mg, 488.65 mmol, 1 eq.) was added to a mixed solvent of 2 ml of MC and 400 ml of TFA. And it was stirred at 20° C. for 15 hours. The reaction was confirmed by TLC (MC:MeOH=10:1, Rf=0.3). SM was completely consumed. After adjusting the pH to 7-8 with sodium hydrogen carbonate (NaHCO$_3$ soln.) in the reaction solution, and purified water and MC were added. And it was extracted three times. The organic layer was washed back with brine solution (Brine soln.), dehydrated with sodium sulfate (Na$_2$SO$_4$), filtered, and concentrated to obtain the target compound 13.

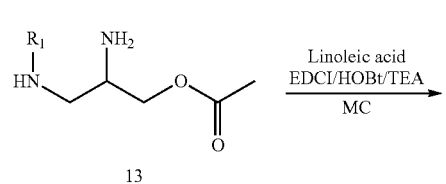

-continued

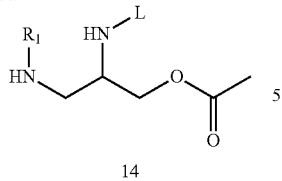

14

Compound 13 synthesized in Reaction 3e (181 mg, 488.44 mmol, 1 eq.), Linoleic acid (1.2 eq.), EDCI (1.2 eq.), HOBt (1.2 eq.) and TEA (4 eq.) were added to 100 ml of MC in the $N_2$-purge. And it was stirred at 20~25° C. for 16 hours. The reaction was confirmed by TLC (MC:MeOH=10:1, Rf=0.7). SM was completely consumed. The reaction solution was concentrated and purified by column (PE:EA=1:1→3:1) to obtain the target compound 14 (EC-A44, $R_1$=palmitoyl, yield=9.27%).

[Example 23] Synthesis of Glycerol Derivative (EC-A45)

[Reaction 4a]

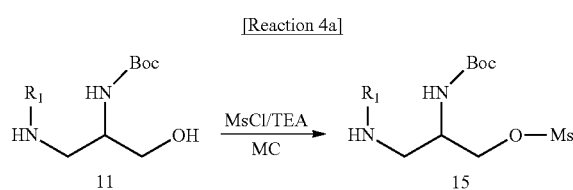

Compound 11 synthesized in Reaction 3c (500 mg, 1.17 mmol, 1 eq.) and TEA (1.1 eq.) were added to 10 ml of MC and cooled to 0° C. And then, methanesulfonyl chloride (1.1 eq.) was slowly added dropwise and stirred at 20° C. for 24 hours. The reaction was confirmed by TLC (PE:EA=2:1, Rf=0.35). Purified water and MC were added to the reaction solution and extracted three times. The organic layer was washed back with brine solution (Brine soln.), dehydrated with sodium sulfate ($Na_2SO_4$) and filtered. And it was purified by a column (PE:EA=1:1) and concentrated to obtain the target compound 15 ($R_1$=palmitoyl, yield=32.05%).

[Reaction 4b]

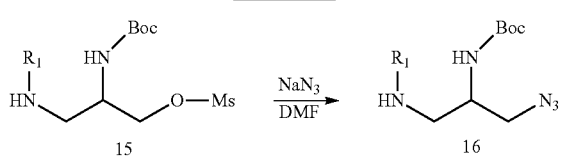

Compound 15 synthesized in Reaction 4a (300 mg, 592.02 mmol, 1 eq.) and sodium azide (2.4 eq.) were added to 6 ml of DMF (dimethylformamide) and stirred at 50° C. for 24 hours. The reaction was confirmed by TLC (PE:EA=2:1, Rf=0.35). SM was completely consumed. After adjusting the pH of 9 or more with purified water and sodium hydrogen carbonate ($NaHCO_3$ soln.) to the reaction solution, added EA to extract three times. The organic layer was washed back with brine solution (Brine soln.), dehydrated with sodium sulfate ($Na_2SO_4$) and filtered. And it was purified by a column (PE:EA=1:1) and concentrated to obtain the target compound 16 ($R_1$=palmitoyl).

[Reaction 4c]

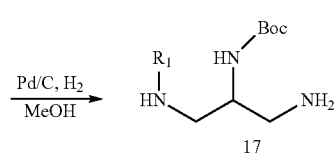

Compound 16 synthesized in Reaction 4b (300 mg, 661.29 mmol, 1 eq.) and Pd/C (300 mg) were added to 10 ml of MeOH in the $N_2$-purge. And then, it was degassed several times with $H_2$, and stirred for 16 hours while maintaining 20 psi of $H_2$ at 20° C. The reaction was confirmed by TLC (MC:MeOH=10:1, Rf=0.25). SM was completely consumed. The reaction was confirmed by LC-MS (EW2692-141-P1A). When the reaction was complete, it was removed by filtration and concentrated to obtain the target compound 17 ($R_1$=palmitoyl).

[Reaction 4d]

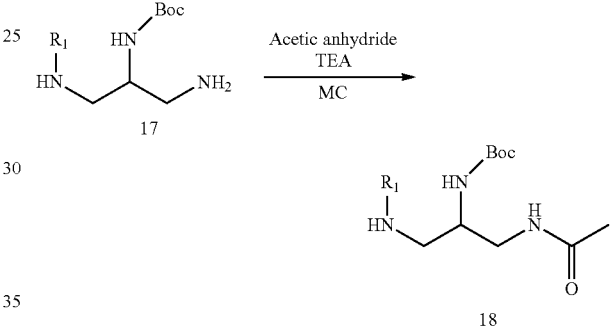

Compound 11 synthesized in Reaction 4c (3000 mg, 701.49 mmole, 1 eq.) was added to 3 ml of MC. And after adding acetic anhydride (1.2 eq.) and TEA (2 eq.) at 0° C., the mixture was stirred at 20° C. for 16 hours. The reaction was confirmed by TLC (MC:MeOH=20:1, Rf=0.3). SM was completely consumed. Purified water and MC were added to the reaction solution and extracted three times. The organic layer was washed back with brine solution (Brine soln.), dehydrated with sodium sulfate ($Na_2SO_4$) and filtered. And it was purified by a column (MC:MeOH=20:1) and concentrated to obtain the target compound 18 (R1=palmitoyl).

[Reaction 4e]

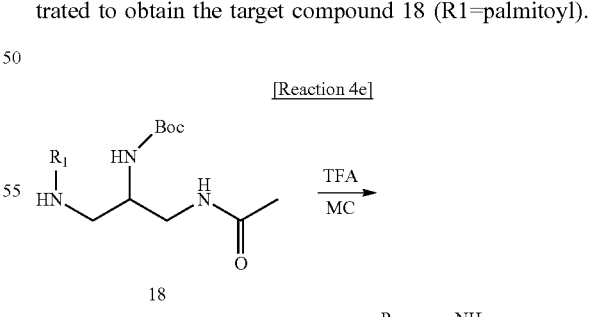

Compound 18 synthesized in Reaction 4d (50 mg, 106.45 mmol, 1 eq.) was added to a mixed solvent of 2 ml of MC and 200 ml of trifluoroacetic acid (TFA) and stirred at 20° C. for 10 hours. The reaction was confirmed by TLC (MC:MeOH=10:1, Rf=0.3). SM was completely consumed. It was adjusted the pH to 7-8 with sodium hydrogen carbonate (NaHCO₃soln.) to the reaction solution and added purified water and MC and extracted three times. The organic layer was washed back with brine solution (Brine soln.), dehydrated with sodium sulfate (Na₂SO₄), filtered, and concentrated to obtain the target compound.

[Reaction 4f]

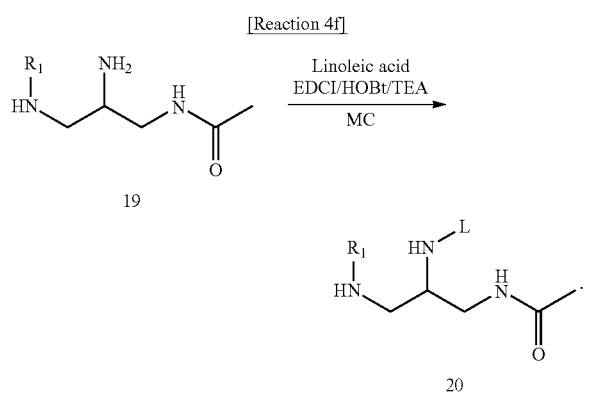

Compound 19 synthesized in Reaction 4e (40 mg, 108.23 mmol, 1 eq.), Linoleic acid (1.2 eq.), EDCI (1.2 eq.), HOBt (1.2 eq.) and TEA (4 eq.) were added to 1 ml of MC in the N₂-purge, and stirred at 20~25° C. for 16 hours. The reaction was confirmed by TLC (MC:MeOH=10:1, Rf=0.5). SM was completely consumed. The reaction solution was concentrated and purified by column (MC:MeOH=15:1) to obtain the target compound 20 (EC-A45, R₁=palmitoyl, yield=14.16%).

[Example 24] Synthesis of Glycerol Derivative (EC-A07)

[Reaction 5a]

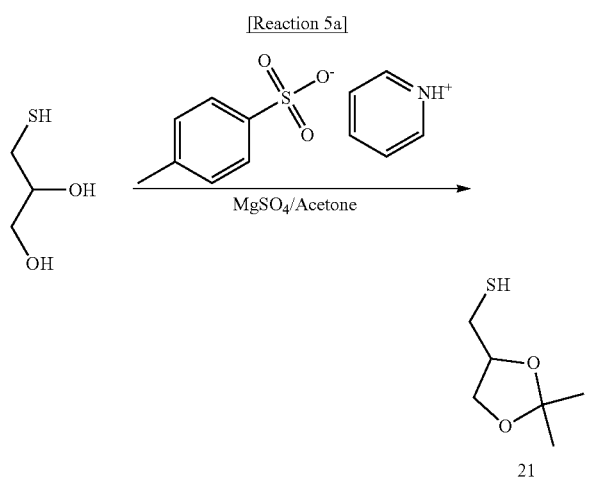

1-Thioglycerol (2 g, 18.49 mmol, 1 eq.) as starting material, pyridinium p-toluenesulfonate (0.1 eq.) and magnesium sulfate (MgSO₄, 1.5 eq.) were added to 40 ml of acetone in the N₂-purge. The reaction was confirmed by TLC (PE:EA=5:1). SM was completely consumed. The reaction solution was filtered, concentrated, and purified by column (PE:EA=100:1→50:1) to obtain the target compound 21 (yield=14.16%).

[Reaction 5b]

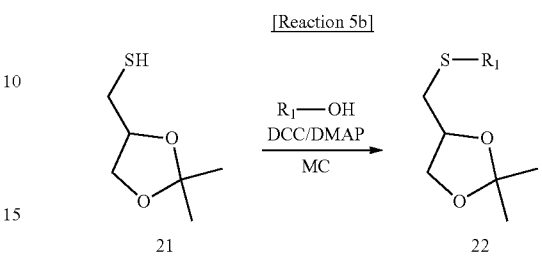

Compound 21 synthesized in Reaction 5a (963.39 mg, 6.5 mmole, 1 eq.), R₁—OH (1.2 eq.), DCC (1.4 eq.) and DMAP (0.2 eq.) were added to 1 ml of MC, and stirred at 20~25° C. for 18 hours. The reaction was confirmed by TLC (MC:MeOH=20:1). SM was completely consumed. The reaction solution was concentrated and purified by column (PE:EA=100:1→20:1) to obtain the target compound 22 (R₁=palmitoyl, yield=75.6%).

[Reaction 5c]

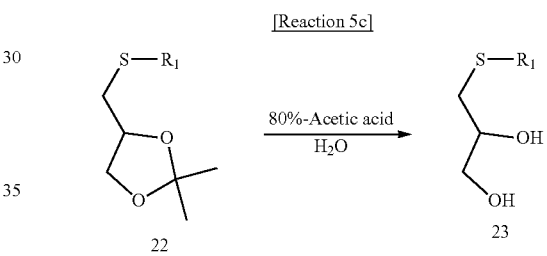

Compound 22 synthesized in Reaction 5b (963.39 mg, 6.5 mmole, 1 eq.) and acetic acid (400 ml) were added to 100 ml of purified water and stirred at 100° C. for 10 minutes. The reaction was confirmed by TLC (MC:MeOH=20:1). SM was completely consumed. The reaction solution was concentrated and recrystallized from 10 ml of petroleum ether to obtain the target compound 23 (R₁=palmitoyl, yield=90.13%).

[Reaction 5d]

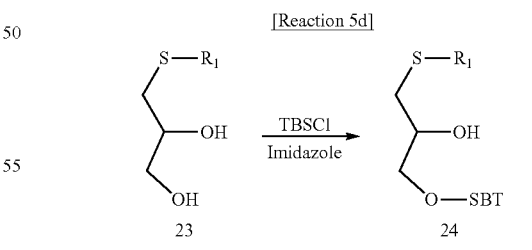

Compound 23 synthesized in Reaction 5c (300 mg, 865.63 mmole, 1 eq.), tert-Butyldimethylsilyl chloride (TBSCl, 1 eq.) and imidazole (4 eq.) were added to 6 ml of MC and stirred at 25° C. for 2 hours. The reaction was confirmed by TLC (PE:EA=5:1). SM was completely consumed. The reaction solution was concentrated and purified by column (PE:EA=5:1) to obtain the target compound 24 (R₁=palmitoyl, yield=52.39%).

[Reaction 5e]

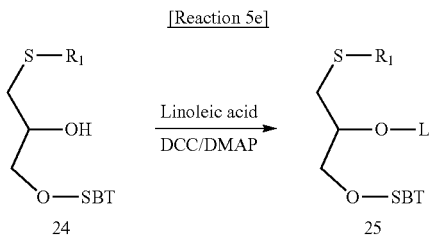

Compound 24 synthesized in Reaction 5d (219.1 mg, 475.44 mmole, 1 eq.), Linoleic acid (1.2 eq.), DCC (1.2 eq.) and DMAP (0.2 eq.) were added to 3 ml of MC, and stirred at 20~25° C. for 18 hours. The reaction was confirmed by TLC (MC:MeOH=20:1). SM was completely consumed. The reaction solution was concentrated and purified by column (PE:EA=10:1) to obtain the target compound 25 (R1=palmitoyl, yield=44.2%).

[Reaction 5f]

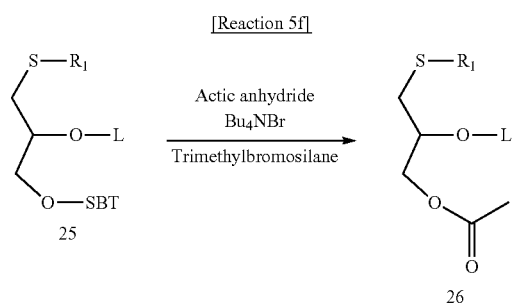

Compound 25 synthesized in Reaction 5e (50 mg, 69.13 mmole, 1 eq.), acetic anhydride (3 eq.), tetra-n-butylammonium bromide (2 eq.) and trimethyl bormosilane (1.5 eq.) were added to 2 ml of MC, and stirred at 50° C. for 18 hours. The reaction was confirmed by TLC (PE:EA=10:1). SM was completely consumed. The reaction solution was concentrated and purified by column (PE:EA=10:1) to obtain the target compound 26 (EC-A07, R1=palmitoyl, yield=52.77%).

[Example 25] Synthesis of Glycerol Derivative (EC-A12)

[Reaction 6a]

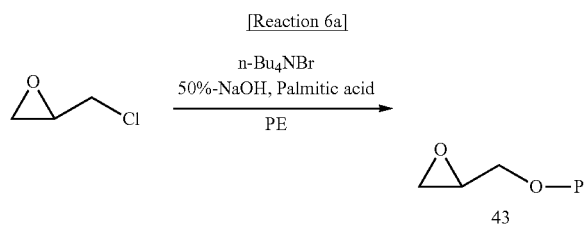

Glycidyl chloride (832.68 mg, 9.0 mmol, 1.8 eq.) as starting material, palmitic acid (1 eq.), Sodium hydroxide (NaOH, 1.8 eq.) and tetra-normal-butylammoniumbromide (n-Bu4NBr, 0.05 eq.) as catalyst were added to 1.5 ml of petroleum ether (PE) in the $N_2$-purge. And the temperature was raised to 50° C. and stirred for 5 hours. The reaction solution was diluted with 30 ml of PE and then filtered. The organic layer was dehydrated with sodium sulfate ($Na_2SO_4$), filtered and concentrated. And it was purification by flash column (PE:EA (ethyl acetate)=50:1) to obtain the target compound 43 (P=palmitoyl, yield=63.65%).

[Reaction 6b]

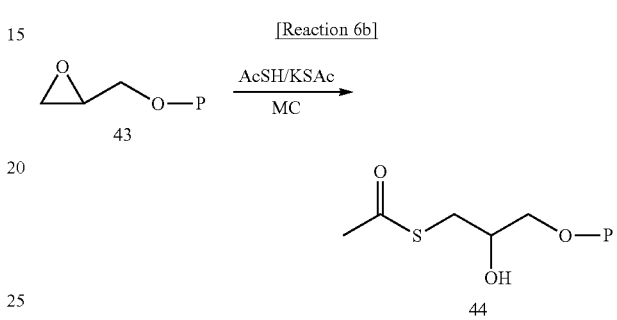

Compound 43 synthesized in Reaction 6a (200 mg, 640.02 mmole, 1 eq.) and potassium thioacetate (KSAc, 0.25 eq.) were dissolved in 2 ml of MC. Thioacetic acid (AcSH, 2.5 eq.) was added to the dissolved solution, and strongly stirred at 15° C. for 65 hours. The reaction was confirmed by TLC (PE:EA=5:1). When the reaction was complete, the reaction solution was concentrated and purified by column (PE:EA=3:1) to obtain the target compound 44 (P=palmitoyl, yield=44.23%).

[Reaction 6c]

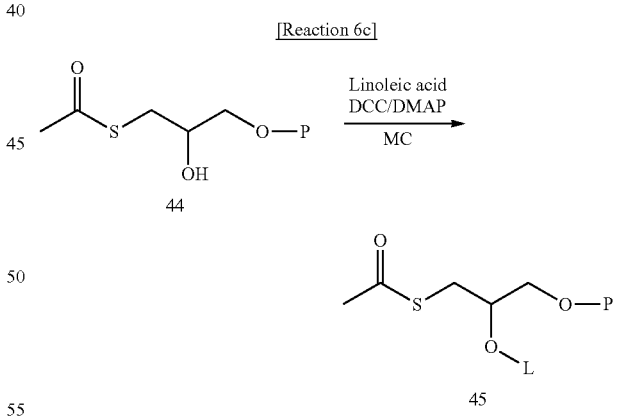

Compound 44 synthesized in Reaction 6d (40 mg, 102.93 mmole, 1 eq.), linoleic acid (1.5 eq.), DCC (1.05 eq.) and DMAP (0.1 eq.) were added to 600 ml of MC, and stirred at 15° C. for 14 hours. The reaction was confirmed by TLC (PE:EA=10:1). When the reaction was complete, it was filtered and extracted with MC and purified water. And then, it was removed water with sodium sulfate ($Na_2SO_4$) and concentrated the organic layer. It was purified by column (PE:EA=3:1) to obtain the target compound 45 (EC-A12, P=palmitoyl, L=linoleoyl, yield=20.82%).

[Example 26] Synthesis of Glycerol Derivative (EC-A05)

[Reaction 7a]

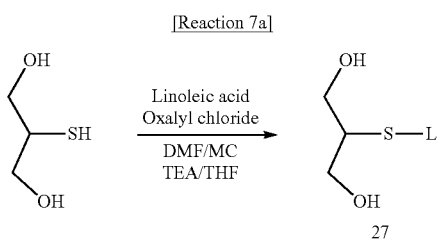

Linoleic acid (588.9 mg, 2.1 mmole, 1 eq.) was added to 10 ml of anhydrous MC. Oxalyl chloride (Cl—CO—CO—Cl, 2 eq.) was dissolved in 1.1 ml of MC, and added to the reaction mixture, and stirred. A solution of 20 ml of MC and DMF (0.1 eq.) was added to the reaction mixture and stirred at 20° C. for 1 hour. The reaction was confirmed by TLC (PE:EA=5:1, Rf=0.3). When the reaction was complete, 627.67 mg of linoleic chloride, a crude product obtained by concentrating the reaction product, was directly used in the next step. Linoleic chloride synthesized above was added to 5 ml of THF at 0-10° C. and stirred. While maintaining 0-10° C., a solution of the starting material, 2-mercapto-1,3-propanediol (454.27 mg, 4.2 mmole, 2 eq.) and TEA (2 eq.) were added to 15 ml of THF, and added it to the above mixture. And then it was stirred at the same temperature for 1 hour. The reaction was confirmed by TLC (MC: MeOH=20:1, Rf=0.2). When the reaction was complete, the reaction solution was diluted with 20 ml of Hex (hexane), filtered, and concentrated. After dissolving in 10 ml of chloroform, it was washed with purified water. And then, the organic layer was dehydrated with sodium sulfate ($Na_2SO_4$), filtered, and concentrated. It was purified by column (PE:EA=1:1) to obtain the target compound 27 (L=linoleoyl, yield=59.05%).

[Reaction 7b]

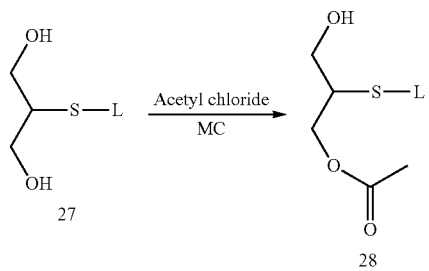

Compound 27 synthesized in Reaction 7a (300 mg, 809.52 mmol, 1 eq.) and TEA (1 eq.) were added to 9 ml of MC, and acetyl chloride (0.8 eq.) was slowly added dropwise at −10~0° C. The reaction solution was stirred at −10~0° C. for 15 minutes. The reaction was confirmed by TLC (PE:EA=3:1, Rf=0.5). When about 50% of SM remained, the reaction was terminated. Purified water and MC are added at 0° C. and extracted three times. The organic layer was washed back with brine solution (Brine soln.), dehydrated with sodium sulfate ($Na_2SO_4$), filtered, and concentrated. It was purified by column (PE:EA=3:1) to obtain the target compound 28 (yield=18.86%).

[Reaction 7c]

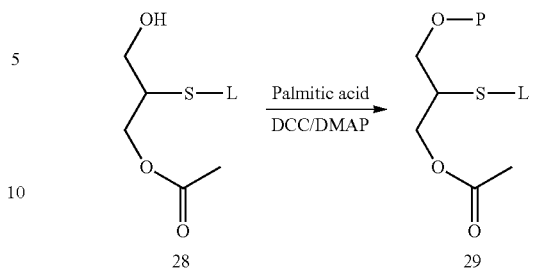

Compound 28 synthesized in Reaction 7b (60 mg, 145.41 mmole, 1 eq.), palmitic acid (1.05 eq.), DCC (1.05 eq.) and DMAP (0.1 eq.) were added to 600 ml of MC, and stirred at 20~25° C. for 16 hours. The reaction was confirmed by TLC (PE:EA=10:1, Rf=0.5). SM was completely consumed. The reaction solution was concentrated and purified by column (PE:EA=10:1) to obtain the target compound 29 (EC_A05, P=palmitoyl, L=linoleoyl, yield=24.1%).

[Example 27] Synthesis of Glycerol Derivative (EC-A60)

[Reaction 8a]

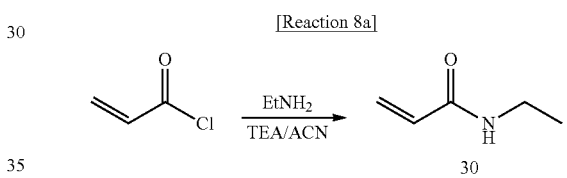

Ethanamine (1.99 g, 44.2 mmole, 1 eq.) and TEA (5 eq.) were added to 140 ml of acetonitrile (ACN), and acryloyl chloride (2.5 eq.) as starting material was slowly added dropwise at 0° C., and stirred at 20° C. for 16 hours. The reaction was confirmed by TLC (PE:EA=1:1). SM was completely consumed. The reaction solution was diluted with EA, washed sequentially with 1N—HCl and $NaHCO_3$, and then once more washed with brine solution (brine soln.). And it was dehydrated with sodium sulfate ($Na_2SO_4$), filtered, and concentrated. It was purified by column (PE:EA=20:1→3:1) to obtain the target compound 30 (yield=58.43%).

[Reaction 8b]

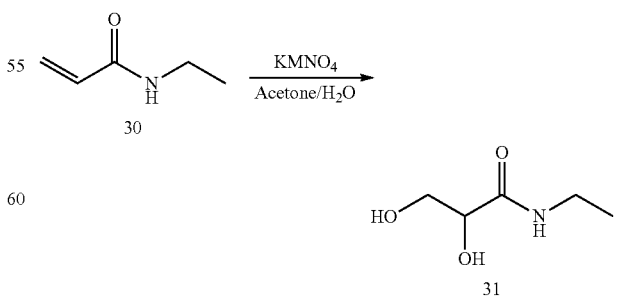

Potassium permanganate ($KMNO_4$, 1.1 eq.) was dissolved to 54 ml of acetone and 36 ml of purified water, and cooled to −50° C. And compound 30 synthesized in Reaction 8a (2.5 g, 25.22 mmole, 1 eq.) was slowly added dropwise thereto. It was stirred at the same temperature for 10 minutes, and the temperature was gradually increased to 20° C. over 30 minutes. The reaction was confirmed by TLC (MC:MeOH=10:1). SM was completely consumed. The reaction solution was filtered and concentrated to obtain the target compound 31.

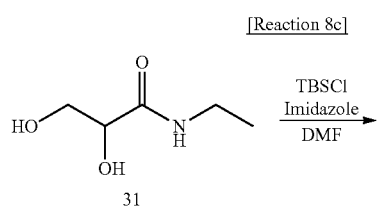

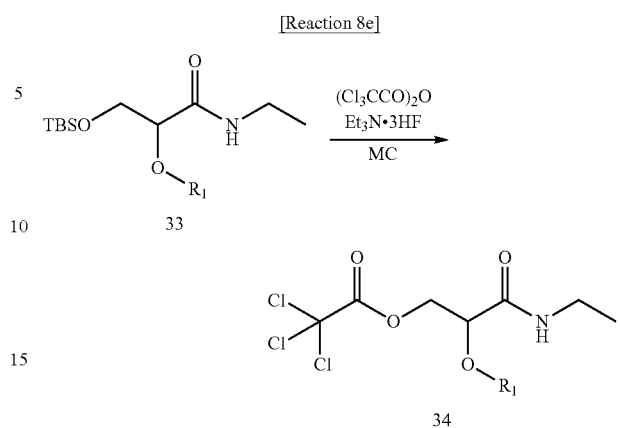

Compound 31 synthesized in Reaction 8b (2.2 g, 16.52 mmole, 1 eq.), tert-Butyldimethylsilyl chloride (TBSCl, 1.2 eq.) and imidazole (2 eq.) were added to 12 ml of N,N-dimethylformamide (DMF), and stirred at 20° C. for 3 hours. The reaction was confirmed by TLC (MC:MeOH=10:1, Rf=0.65). SM was completely consumed. Purified water and EA were added to the reaction solution and extracted three times. The organic layer was more washed back with brine solution (Brine soln.), dehydrated with sodium sulfate (Na$_2$SO$_4$), filtered, and concentrated. It was purified by column (PE:EA=20:1→2:1) to obtain the target compound 32 (yield=28.14%).

Compound 33 synthesized in Reaction 8d (850 mg, 1.67 mmole, 1 eq.), triethylamine trihydrofluoride (2 eq.) and trichloroacetic anhydride (9 eq.) were added to 2 ml of MC at 25~30° C. in the N$_2$-purge. The reaction solution was stirred at 80° C. for 2.5 hours. The reaction was confirmed by TLC (PE:EA=10:1, Rf=0.43). SM was completely consumed. The reaction solution was concentrated and purified by column (PE:EA=50:1→5:1) to obtain the target compound 34 (R$_1$=linoleoyl, yield=81.4%).

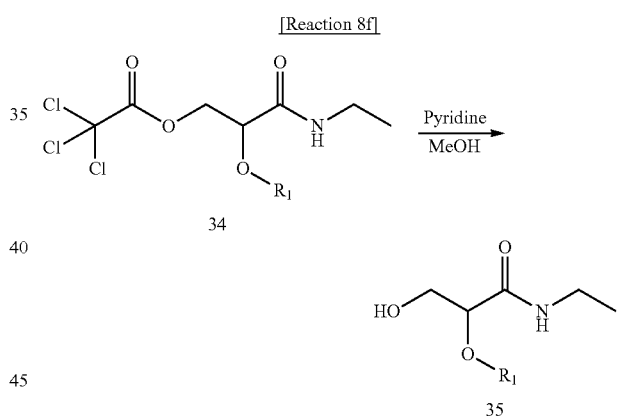

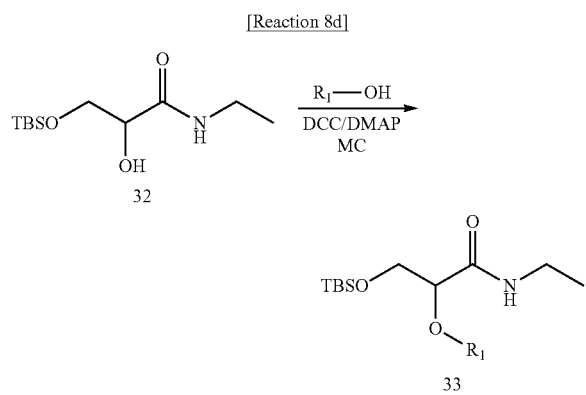

Compound 32 synthesized in Reaction 8c (750 mg, 3.03 mmole, 1.05 eq.), R$_1$—OH (R$_1$=carbonyl group having 2 to 18 carbon atoms, 1 eq.), DCC (1 eq.) and DMAP (0.1 eq.) were added to 8 ml of MC, and stirred at 20° C. for 16 hours. The reaction was confirmed by TLC (PE:EA=3:1, Rf=0.75). SM was completely consumed. The reaction solution was concentrated and purified by column (PE:EA=50:1→5:1) to obtain the target compound 33 (R$_1$=linoleoyl, yield=58.45%).

1 ml of pyridine and compound 34 synthesized in Reaction 8e (800 mg, 1.48 mmol, 1 eq.) were added to 10 ml of MeOH, and stirred at 25° C. for 1 hour. The reaction was confirmed by TLC (PE:EA=50:1, Rf=0.22). SM was completely consumed. The reaction solution was concentrated and purified by column (PE:EA=50:1→2:1) to obtain the target compound 35 (R$_1$=linoleoyl, yield=56.37%).

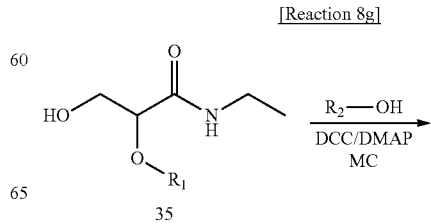

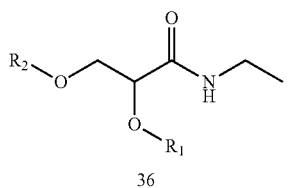

Compound 35 synthesized in Reaction 8f (320 mg, 808.96 mmole, 1.2 eq.), $R_2$—OH($R_2$=carbonyl group having 2 to 18 carbon atoms, 1 eq.), DCC (1.2 eq.) and DMAP (0.2 eq.) were added to 4 ml of MC, and stirred at 20° C. for 16 hours. The reaction was confirmed by TLC (PE:EA=5:1, Rf=0.58). SM was completely consumed. The reaction solution was concentrated and purified by column (PE:EA=50:1→5:1) to obtain the target compound 36 (EC-A60, $R_1$=linoleoyl, $R_2$=palmitoyl, yield=77.89%).

[Example 28] Synthesis of Glycerol Derivative (EC-60A)

In substantially the same manner as in Example 27, a glycerol derivative compound was synthesized. The structure of the target compound (EC-60A) was that in compound 36, $R_1$ was palmitoyl and $R_2$ was linoleoyl, and the yield of the final synthesis step was 62.14%.

[Example 29] Synthesis of Glycerol Derivative (EC-A59)

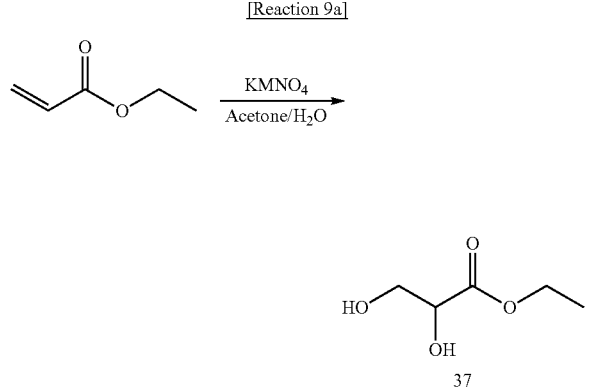

Potassium permanganate (KMNO$_4$, 1.1 eq.) was added to 45 ml of acetone and 30 ml of purified water and cooled to −50° C. And ethyl acrylate (2 g, 19.976 mmole, 1 eq.) as starting material was slowly added dropwise thereto. It was stirred at the same temperature for 10 minutes, and the temperature was gradually increased to 20° C. over 30 minutes. The reaction was confirmed by TLC (MC:MeOH=10:1). SM was completely consumed. After filtering the reaction product, it was extracted three times with purified water, brine solution (brine soln.) and EA. And dehydration was performed with magnesium sulfate (MgSO$_4$), filtered, and concentrated to obtain the target compound 37 (yield=39%).

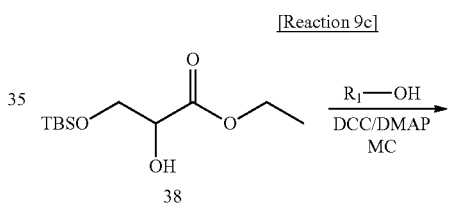

Compound 37 synthesized in Reaction 9a (1.05 g, 7.83 mmole, 1 eq.), tert-Butyldimethylsilyl chloride (TBSCl, 1.2 eq.) and imidazole (2 eq.) were added to 20 ml of MC, and stirred at 20° C. for 3 hours. The reaction was confirmed by TLC (Hex:EA=1:1 or 9:1, Rf=0.4). SM was completely consumed. Purified water and MC were added to the reaction solution, extracted three times, and once more washed with brine solution (brine soln.). And it was dehydrated with sodium sulfate (Na$_2$SO$_4$), filtered, and concentrated. It was purified by a column (Hex:EA=13:1) to obtain the target compound 38 (yield=72%).

Compound 38 synthesized in Reaction 9b (640 mg, 2.58 mmole, 1.05 eq.), $R_1$—OH($R_1$=carbonyl group having 2 to 18 carbon atoms, 1 eq.), DCC (1.05 eq.) and DMAP (0.1 eq.) were added to 6.5 ml of MC, and stirred at 20° C. for 16 hours. The reaction was confirmed by TLC (Hex:EA=13:1). SM was completely consumed. The reaction solution was concentrated and purified by column (PE:EA=200:1→100:1) to obtain the target compound 39 ($R_1$=linoleoyl, yield 68.52%).

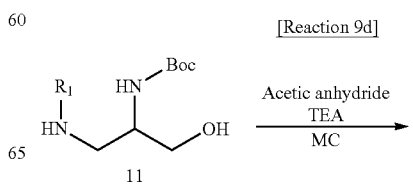

-continued

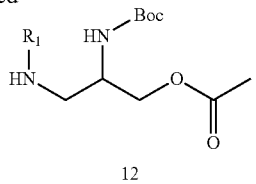

12

Compound 39 synthesized in Reaction 9c (800 mg, 1.57 mmole, 1 eq.), triethylamine trihydrofluoride (2 eq.) and trichloroacetic anhydride (9 eq.) were added to 5 ml of MC at 25~30° C. in the $N_2$-purge. The reaction solution was stirred at 80° C. for 2.5 hours. The reaction was confirmed by TLC (PE:EA=20:1, Rf=0.43). SM was completely consumed. The reaction solution was concentrated to obtain the target compound 40 ($R_1$=linoleoyl, 620 mg, crude).

[Reaction 9e]

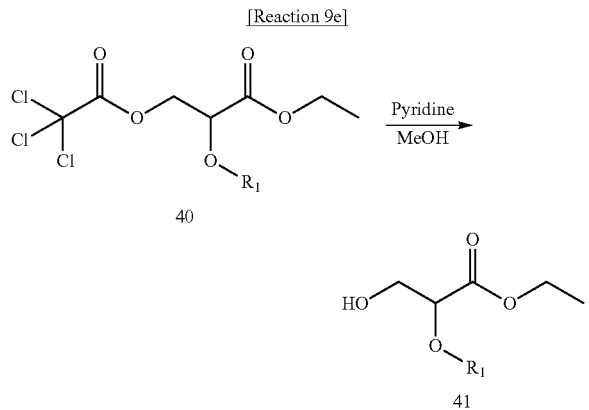

2 ml of pyridine and compound 40 synthesized in Reaction 9d (2 g, 3.69 mmol, crude) was added to 20 ml of MeOH, and stirred at 25° C. for 1 hour. The reaction was confirmed by TLC (PE:EA=10:1, Rf=0.42). SM was completely consumed. The reaction solution was concentrated. EA and purified water was added and extracted three times. And it was dehydrated with sodium sulfate ($Na_2SO_4$) and concentrated. It was purified by column (PE:EA=100:1→20:1) to obtain the target compound 41 ($R_1$=linoleoyl, yield=38.27%).

[Reaction 9f]

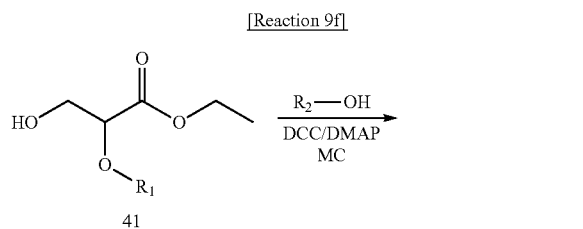

Compound 41 synthesized in Reaction 9e (200 mg, 504.34 mmole, 1.2 eq.), $R_2$—OH($R_2$=carbonyl group having 2 to 18 carbon atoms, 1 eq.), DCC (1.21 eq.) and DMAP (0.2 eq.) were added to 2 ml of MC, and stirred at 20° C. for 16 hours. The reaction was confirmed by TLC (PE:EA=10:1, Rf=0.68). SM was completely consumed. The reaction solution was concentrated and purified by column (PE:EA=200:1→20:1) to obtain the target compound 42 (EC-A59, $R_1$=linoleoyl, $R_2$=palmitoyl, yield=86.19%).

[Example 30] Synthesis of Glycerol Derivative (EC-59 A)

In substantially the same manner as in Example 29, a glycerol derivative compound was synthesized. The structure of the target compound (EC-59A) was that in compound 42, $R_1$ was palmitoyl and $R_2$ was linoleoyl, and the yield of the final synthesis step was 80.94%.

[Experimental Example 1] LPS-Induced IL-6 Secretion Reduction

In DMEM (Hyclone, Thermo Scientific) medium to which 10% Fetal Bovine Serum was added, RAW264.7 cells, a mouse macrophage family, were suspended at a concentration of $1\times10^5$ cells/ml, and the cells were maintained in a 5% $CO_2$ humidified incubator at 37° C., and cultured. The cultured RAW264.7 cells were inoculated into a 48 well plate by $5\times10^4$ cells/ml and stabilized for 15 hours. Then, the culture solution was treated with a glycerol derivative compounds of the type shown in Table 2 and 3 below for 1 hour and then was treated with 1 μg/ml of Lipopolysaccaride (LPS) of a cell stimulator, and subsequent further incubation was conducted for 24 hours. Thereafter 0.5 ml of the culture supernatant was collected for each well and centrifuged (at 3000 rpm, 5 minutes) to recover the supernatant. The IL-6 level in the recovered supernatant was measured according to the manual provided by the Mouse IL-6 ELISA set (BD Biosciences). The day before ELISA was carried out, the IL-6 capture antibody was diluted in phosphate buffered saline, coated on a microwell, and then stored at 4° C. overnight. Each well was washed three times with a washing buffer solution and then blocked with 2% Bovine Serum Albumin (BSA) for 1 hour at room temperature. After washing with buffer solution three times, 100 μl of sample was dispensed into each well and left at room temperature for 2 hours. Detection antibody which was washed 3 times with washing buffer solution and diluted was dispensed into each well and allowed to react at room temperature for 1 hour and left at room temperature for 1 hour. Thereafter, the secondary HRP conjugated antibody was reacted at room temperature for 30 minutes, washed three times with a washing buffer solution, and treated with 50 μl of stop solution for each well, and then the optical density was measured at 450 nm with an ELISA microplate leader. The results of the expression reduction rate are shown in Table 2 and Table 3 below.

TABLE 2

| | sample | Concentration (μg/ml) | IL-6 concentration (μg/μl, average ± deviation) |
|---|---|---|---|
| 1 | Negative control group | 0 | 0.045 ± 0.001 |
| 2 | DMSO | 1% | 0.045 ± 0.004 |
| 3 | LPS | 1 | 0.262 ± 0.008 |
| 4 | EC-18 | 100 | 0.194 ± 0.011 |
| 5 | EC_A04 | 100 | 0.141 ± 0.016 |
| 6 | EC_A04_2 | 100 | 0.048 ± 0.003 |
| 7 | EC_A04_3 | 100 | 0.043 ± 0.000 |

TABLE 2-continued

|  | sample | Concentration (μg/ml) | IL-6 concentration (μg/μl, average ± deviation) |
|---|---|---|---|
| 8 | EC_A05 | 100 | 0.164 ± 0.012 |
| 9 | EC_A06 | 100 | 0.168 ± 0.004 |
| 10 | EC_A06A | 100 | 0.180 ± 0.011 |
| 11 | EC_A11 | 100 | 0.257 ± 0.029 |
| 12 | EC_A12 | 100 | 0.245 ± 0.003 |
| 13 | EC A44 | 100 | 0.197 ± 0.031 |
| 14 | EC_A59 | 100 | 0.174 ± 0.033 |
| 15 | EC_A59A | 100 | 0.168 ± 0.044 |
| 16 | EC_A60 | 100 | 0.187 ± 0.000 |
| 17 | EC_A60A | 100 | 0.178 ± 0.001 |
| 18 | EC_A73 | 100 | 0.183 ± 0.000 |
| 19 | EC_A73A | 100 | 0.130 ± 0.006 |
| 20 | EC_A74 | 100 | 0.187 ± 0.006 |
| 21 | EC_A75 | 100 | 0.170 ± 0.071 |
| 22 | EC_A76 | 100 | 0.167 ± 0.019 |
| 23 | EC_A77 | 100 | 0.171 ± 0.032 |

TABLE 3

|  | sample | Concentration (μg/ml) | IL-6 concentration (pg/μl, average ± deviation) |
|---|---|---|---|
| 2 | DMSO | 1% | 0.588 ± 0.003 |
| 3 | LPS | 1 | 1.526 ± 0.077 |
| 4 | EC-18 | 100 | 1.159 ± 0.036 |
| 5 | EC_A104 | 100 | 1.293 ± 0.000 |
| 6 | EC_A105 | 100 | 1.163 ± 0.074 |
| 7 | EC_A106 | 100 | 1.139 ± 0.010 |
| 8 | EC_A107 | 100 | 1.462 ± 0.180 |
| 9 | EC_A111 | 100 | 1.562 ± 0.127 |
| 10 | EC A112 | 100 | 1.312 ± 0.170 |
| 11 | EC_A113 | 100 | 1.417 ± 0.159 |
| 12 | EC_A114 | 100 | 1.394 ± 0.072 |

Figure 2:
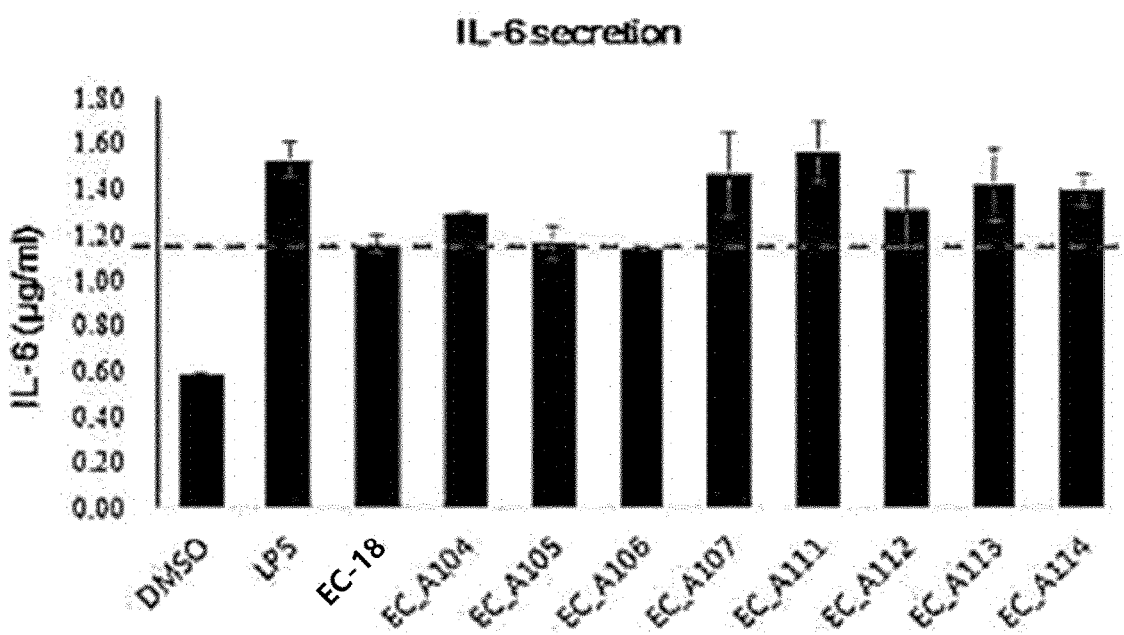

FIG. 1 and FIG. 2 are graphs which show the values in Table 2 and Table 3 above, which shows the degree of IL-6 secretion induced by the LPS. As shown in Table 2, Table 3, FIG. 1 and FIG. 2, it was confirmed that when RAW264.7 cells were treated with LPS, an inflammation-induced factor, the secretion of IL-6, a inflammatory cytokines, was increased by about six to ten times compared to the negative control group. When EC-18 (1-palmitoyl-2-linoleoyl-3-acetylglycerol, PLAG) compound, a substance that inhibits the expression of inflammatory cytokines, was added, IL-6 expression was decreased about 30% compared to the LPS-treated group, and in the case of the glycerol derivative compound of the present invention, A04, A04-2, A04-3, A05, A06, A06A, A44, A59, A59A, A60, A60A, A73, A73A, A74, A75, A76, A77, A105, A106 are a derivative similar to or more inhibiting IL-6 expression as EC-18 (PLAG), and it was confirmed that IL-6 cytokine secretion was reduced in RAW264.7 cells by as little as 30% and as much as 50%. In particular, compounds A04-2 and A04-3 showed the level of IL-6 expression in the negative control group not treated with LPS, and completely inhibited the activity of LPS.

[Experimental Example 2] IL-6-Induced STAT3 Activity Reduction

Two experiments were conducted as a method of confirming STAT3 activity. First, HEK-Blue™ IL-6 cells were used to confirm the degree of activity by STAT3-induced SEAP (secreted embryonic alkaline phosphatase) expression. Second, this is a method to check the degree of STAT3 activity by injecting the pGL4.47 [luc2P/SIE/Hygro] vector containing the sis-inducible element that binds to STAT3 into RAW264.7 cells. Table 4 below confirmed the STAT3 activity inhibitory ability of the derivative compound of the present invention using the first method.

In DMEM (Hyclone, Thermo Scientific) medium to which 10% Fetal Bovine Serum was added, HEK-Blue™ IL-6 cells were cultured at a concentration of $1 \times 10^5$ cells/ml, and the cells were maintained in a 5% $CO_2$ humidified incubator at 37° C., and cultured. The cultured HEK-Blue™ IL-6 cells were inoculated by $1 \times 10^5$ cells/ml, and treat with a glycerol derivative compounds of the type shown in Table 3 below in the culture solution for 1 hour, and then IL-6 (5 ng/ml) was further incubated for 24 hours for STAT3 activity. Thereafter, the culture supernatant was collected for each well and centrifuged (at 3000 rpm, 5 minutes) to recover the supernatant. The SEAP expression level in the recovered supernatant was mixed with Quanti blue reagent and the supernatant at a ratio of 1:10 and left at 37° C. for about 30 minutes. Then, the SEAP concentration was confirmed at 650 nm wavelength using a spectrophotometer, and the results thereof are shown in Table 4 below.

TABLE 4

|  | sample | Concentration (μg/ml) | STAT3 activity SEAP expression(%) (average ± deviation) |
|---|---|---|---|
| 1 | Negative control group | 0 | 100 |
| 2 | IL-6 | 5 ng/ml | 228.8 ± 17.0 |
| 3 | EC_18 | 100 | 173.0 ± 7.9 |
| 4 | EC_A04 | 100 | 177.2 ± 18.4 |
| 5 | EC_A04_2 | 100 | 85.4 ± 9.4 |
| 6 | EC_A04_3 | 100 | 85.9 ± 6.4 |
| 7 | EC_A05 | 100 | 201.6 ± 34.6 |
| 8 | EC_A06 | 100 | 164.8 ± 16.3 |
| 9 | EC_A11 | 100 | 167.4 ± 9.8 |
| 10 | EC_A12 | 100 | 174.9 ± 12.1 |
| 11 | EC_A44 | 100 | 236.5 ± 55.9 |

Figure 3:
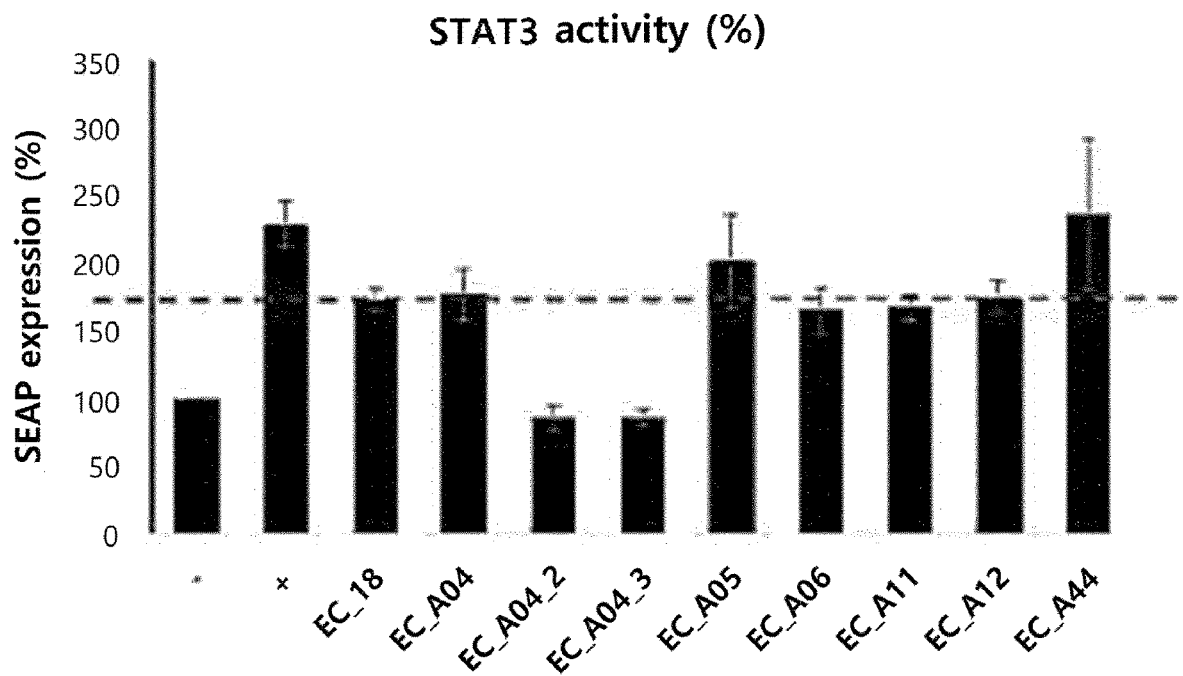
FIGS. 3 and 4 are graphs showing the degree of STAT3 activity induced by IL-6 according to another embodiment of the present invention.

FIG. 3 is a graph which shows the values in Table 4 above, which shows the degree of STAT3 activity induced by the IL-6. As shown in Table 4 and FIG. 3, it was confirmed that when IL-6 cytokine was treated in HEK-Blue™ IL-6 cells, the STAT3 activity was increased by about 2.3 times compared to the negative control group. The EC-18 (PLAG)-treated group decreased STAT3 activity by about 25% compared to the LPS-treated group. In the case of the glycerol derivative compound of the present invention, derivatives that reduce STAT3 activity to a degree similar to EC-18 (PLAG) include A04, A06, and A11 A12, and it was confirmed that most of them reduce STAT3 activity by about 25%. In the case of A04-2 and A04-3, it was confirmed that STAT3 activity by LPS was inhibited as much as that of the negative control without IL-6 treatment.

[Experimental Example 3] IL-6-Induced STAT3 Activity Reduction

In DMEM (Hyclone, Thermo Scientific) medium to which 10% Fetal Bovine Serum was added, RAW264.7 cells were cultured at a concentration of $1 \times 10^5$ cells/ml, and the cells were maintained in a 5% $CO_2$ humidified incubator at 37° C., and cultured. The cultured RAW264.7 cells were inoculated into a 48 well plate by $1 \times 10^5$ cells/ml and stabilized for 18 hours. Thereafter, the pGL4.47 [luc2P/SIE/Hygro] vector containing sis-Inducible Element was mixed with Attractene to induce complex formation at room temperature for 15 minutes. This complex was treated with the cells and then further incubated for 18 hours. Thereafter, the culture solution was treated with a glycerol derivative compounds of the type shown in Table 5 below in the culture solution for 1 hour and then LPS (1 µg/ml) was treated and further incubated for 18 hours for STAT3 activity. Thereafter, the culture supernatant was removed for each well, and the remaining cells were lysed with a cell lysis buffer, and then cell lysate was recovered. 90 µl of luciferase reagent was mixed with 10 µl of the recovered cell lysate, and the degree of fluorescence was confirmed using a luminometer. The results are shown in Table 5 below.

TABLE 5

| | sample | Concentration (µg/ml) | STAT3 activity_ Luciferase activity (average ± deviation) |
|---|---|---|---|
| 1 | Negative control group | 0 | 100.00 ± 0.00 |
| 2 | DMSO | 1% | 73.26 ± 4.54 |
| 3 | LPS | 1 | 857.47 ± 12.13 |
| 4 | EC-18 | 100 | 393.64 ± 46.12 |
| 5 | EC_A59 | 100 | 392.97 ± 40.30 |
| 6 | EC_A59A | 100 | 410.32 ± 5.35 |
| 7 | EC_A60 | 100 | 572.19 ± 40.59 |
| 8 | EC_A60A | 100 | 717.94 ± 25.68 |
| 9 | EC_A73 | 100 | 451.22 ± 166.71 |
| 10 | EC_A73A | 100 | 649.59 ± 274.69 |
| 11 | EC_A74 | 100 | 484.95 ± 29.86 |
| 12 | EC_A75 | 100 | 727.51 ± 117.37 |
| 13 | EC_A76 | 100 | 786.72 ± 202.75 |
| 14 | EC_A77 | 100 | 500.37 ± 63.45 |
| 15 | EC_A104 | 100 | 402.47 ± 55.50 |
| 16 | EC_A105 | 100 | 458.80 ± 20.98 |
| 17 | EC_A106 | 100 | 485.49 ± 6.45 |
| 18 | EC_A107 | 100 | 541.13 ± 98.80 |
| 19 | EC_A111 | 100 | 339.58 ± 20.40 |
| 20 | EC_A112 | 100 | 470.22 ± 13.74 |
| 21 | EC_A113 | 100 | 421.60 ± 29.72 |
| 22 | EC_A114 | 100 | 382.48 ± 54.41 |

Figure 4:
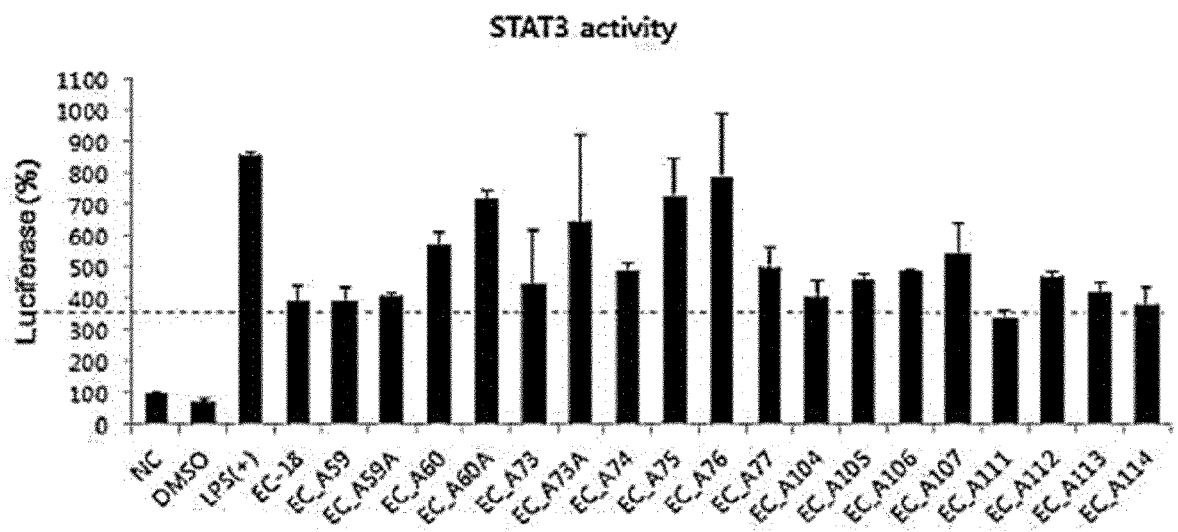

FIG. 4 is a graph which shows the values in Table 5 above, which shows the degree of STAT3 activity induced by the IL-6. As shown in Table 5 and FIG. 4, it was confirmed that when LPS was treated in RAW264.7 cells, the STAT3 activity was increased by about 8.5 times compared to the negative control group, and the EC-18 (PLAG)-treated group decreased the activity by about 50%. In the case of the glycerol derivative compound of the present invention, it was confirmed that there are A59, A59A, A104, A111, A113, and A114 derivatives that reduce STAT3 activity to a degree similar to that of EC-18 (PLAG).

[Experimental Example 4] CXCL8 (IL-8) Expression Reduction in THP-1 Cells

In RPMI (Hyclone, Thermo Scientific) medium to which 10% Fetal Bovine Serum was added, THP-1 cells, a human macrophage family, were suspended at a concentration of $1 \times 10^5$ cells/ml, and the cells were maintained in a 5% $CO_2$ humidified incubator at 37° C., and cultured. The cultured THP-1 cells were inoculated into a 12 well plate by $1 \times 10^6$ cells/ml and stabilized for 30 minutes. Then, the culture solution was treated with a glycerol derivative compounds of the type shown in Table 6 below for 1 hour and then was treated with Gemcitabine (2 µg/ml) of a cell stimulator, and subsequent further incubation was conducted for 24 hours. Thereafter 1.5 ml of the culture supernatant was collected for each well and centrifuged (at 3000 rpm, 5 minutes) to recover the supernatant. The CXCL8 (IL-8) level in the recovered supernatant was measured according to the manual provided by the human IL-8 ELISA set (BD Biosciences). The day before ELISA was carried out, the IL-8 capture antibody was diluted in phosphate buffered saline, coated on a microwell, and then stored at 4° C. overnight. Each well was washed three times with a buffer solution and then blocked with 2% Bovine Serum Albumin (BSA) for 1 hour at room temperature. After washing with washing buffer solution three times, 100 µl of sample was dispensed into each well and left at room temperature for 2 hours. Detection antibody which was washed 3 times with washing buffer and diluted was dispensed into each well and allowed to react at room temperature for 1 hour and left at room temperature for 1 hour. Thereafter, the secondary HRP conjugated antibody was reacted at room temperature for 30 minutes, washed three times with a washing buffer, and treated with 50 µl of stop solution for each well, and then the optical density was measured at 450 nm with an ELISA microplate leader. The results of the expression increase rate are shown in Table 6 below.

TABLE 6

| | sample | Concentration (µg/ml) | CXCL8 [IL-8] concentration (pg/µl, average ± deviation) |
|---|---|---|---|
| 1 | Negative control group | 0 | 7.9 ± 0.0 |
| 2 | Gemcitabine | 2 | 104.6 ± 1.5 |
| 3 | EC_18 | 100 | 79.6 ± 6.0 |
| 4 | EC_A04 | 100 | 124.2 ± 0.5 |
| 5 | EC_A04_2 | 100 | 141.6 ± 0.0 |
| 6 | EC_A04_3 | 100 | 68.5 ± 0.2 |
| 7 | EC_A05 | 100 | 84.6 ± 0.0 |
| 8 | EC_A06 | 100 | 96.8 ± 8.3 |
| 9 | EC_A06A | 100 | 228.7 ± 1.0 |
| 10 | EC_A44 | 100 | 96.8 ± 8.3 |
| 11 | EC_A45 | 100 | 82.0 ± 2.0 |
| 12 | EC_A59 | 100 | 79.6 ± 2.3 |
| 13 | EC_A59A | 100 | 116.6 ± 2.8 |
| 14 | EC_A73A | 100 | 100.9 ± 3.6 |
| 15 | EC_A74 | 100 | 114.4 ± 3.9 |
| 16 | EC_A75 | 100 | 110.9 ± 8.9 |
| 17 | EC_A76 | 100 | 225.9 ± 7.0 |
| 18 | EC_A104 | 100 | 113.6 ± 5.4 |
| 19 | EC_A105 | 100 | 112.3 ± 1.8 |
| 20 | EC_A106 | 100 | 115.7 ± 4.3 |
| 21 | EC_A107 | 100 | 107.6 ± 3.4 |
| 22 | EC_A111 | 100 | 92.0 ± 7.2 |
| 23 | EC_A112 | 100 | 106.5 ± 8.2 |
| 24 | EC_A113 | 100 | 113.1 ± 11.1 |
| 25 | EC_A114 | 100 | 120.2 ± 4.3 |

Figure 5:
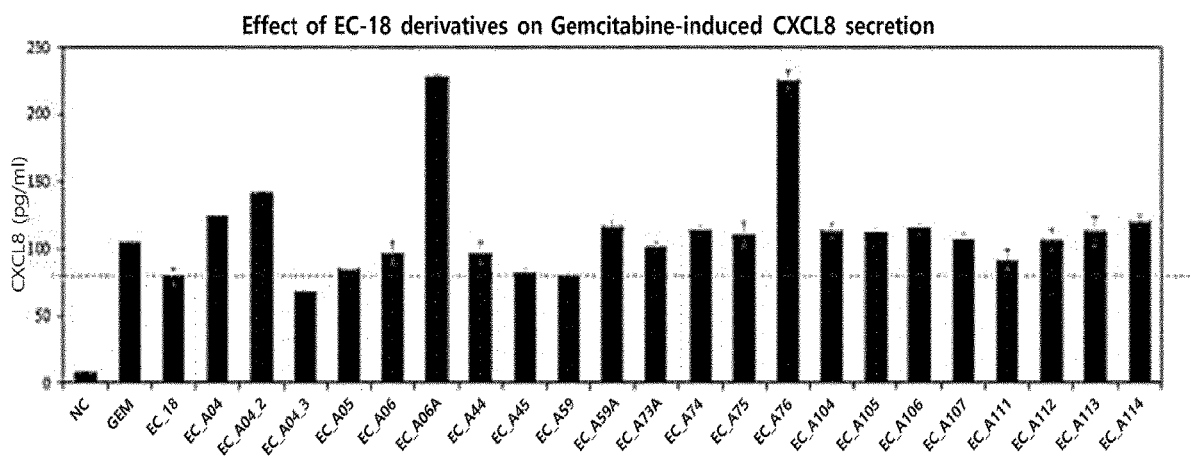
FIG. 5 is a graph showing the degree of CXCL8 (IL-8) expression of THP-1 cells according to another embodiment of the present invention.

FIG. 5 is a graph which shows the values in Table 6 above, which shows the degree of CXCL8 (IL-8) expression. As shown in Table 6 and FIG. 5, it was confirmed that when Gemcitabine, an anticancer drug, was treated in THP-1 cells, the secretion of CXCL8 (IL-8) chemokine, a neutrophil cell recruitment factor, was increased by about 13 times compared to the negative control group. When the EC-18 (PLAG) was treated, it was reduced CXCL8 expression by about 20%. When the treatment of the glycerol derivative compound of the present invention is added, derivatives that reduce the secretion of CXCL8 (IL-8) chemokine to a similar degree to EC-18 (PLAG) include A04-3, A05, A44, and A45. In the case of A04-3, it was confirmed that it was reduced to about 35%.

[Experimental Example 5] Reduction in Migration of HL-60 Cell Line Using Transwell In RPMI (Hyclone, Thermo Scientific) medium to which 10% Fetal Bovine Serum was added, THP-1 cells, a human macrophage family, were subcultured at a concentration of $1 \times 10^5$ cells/ml, and the cells were maintained in a 5% $CO_2$ humidified incubator at 37° C., and cultured. In order to prepare the THP-1 cell culture solution to be treated in the lower well during the transmigration assay, first, the cultured THP-1 cells were inoculated into a 12 well plate by $1\times10^6$ cells/ml and stabilized for 30 minutes. Then, the culture solution was treated with a glycerol derivative compounds of the type shown in Table 7 below for 1 hour and then was treated with Gemcitabine (2 μg/ml) of a cell stimulator, and subsequent further incubation was conducted for 24 hours. Thereafter 1.5 ml of the culture supernatant was collected for each well and centrifuged (at 3000 rpm, 5 minutes) to recover the supernatant. The CXCL8 (IL-8) level in the recovered supernatant was measured according to the manual provided by Cultrex 96 well Laminin Cell Invasion assay. The day before Transmigration assay was carried out, a 1× Lamin I solution was treated in the upper Invasion Chamber and coated. Thereafter, in RPMI (Hyclone, Thermo Scientific) medium to which 10% Fetal Bovine Serum was added, the cultured HL-60 cells were despensed of $5\times10^4$ cells/chamber, and 150 μl of the THP-1 culture supernatant prepared in advance was added to the lower chamber. Thereafter the upper chamber was removed, and the cells were attached to the bottom of the lower chamber by a centrifuge, and then the supernatant was removed. Cell dissociation/Calcein-AM solution was added and reacted for 1 hour. Then, the value obtained using a fluorescence spectroscopy was calculated by converting the number of cells. The results of the reduction in migration of HL-60 cells were shown in Table 7 below.

TABLE 7

| | sample | Concentration (μg/ml) | Number of HL-60 cells migrated through Transwell (Cell Number) |
|---|---|---|---|
| 1 | Negative control group | 0 | 2582.6 |
| 2 | Gemcitabine | 2 | 5022.9 |
| 3 | EC_18 | 100 | 2697.2 |
| 4 | EC_A04 | 100 | 11116.7 |
| 5 | EC_A04_2 | 100 | 4346.3 |
| 6 | EC_A04_3 | 100 | 11646.2 |
| 7 | EC_A05 | 100 | 17283.8 |
| 8 | EC_A06A | 100 | 11719.5 |
| 10 | EC_A44 | 100 | 9320.6 |
| 11 | EC_A45 | 100 | 16343.3 |
| 12 | EC_A59 | 100 | 15130.2 |
| 13 | EC_A59A | 100 | 4714.8 |
| 14 | EC_A73A | 100 | 2527.7 |
| 15 | EC_A75 | 100 | 3140.9 |
| 16 | EC_A76 | 100 | 5338.4 |
| 17 | EC_A104 | 100 | 6901.7 |
| 18 | EC_A111 | 100 | 4899.9 |

Figure 6:
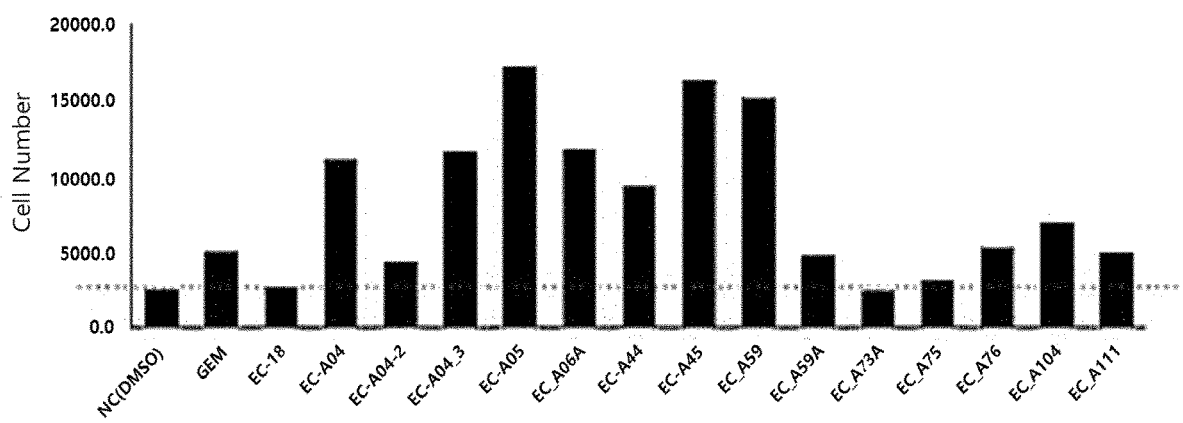
FIG. 6 is a graph showing the degree of the HL-60 cell line migration using Transwell according to another embodiment of the present invention.

FIG. 6 is a graph which shows the values in Table 7 above, which shows the degree of migration of HL-60 cell line using Transwell. As shown in Table 7 and FIG. 6, it was confirmed that when Gemcitabine, an anticancer drug, was treated in THP-1 cells, a neutrophil cell migration was increased by about twice compared to the negative control group. When the EC-18 (PLAG) was treated, the migration of HL-60 cells was reduced to a degree similar to that of the negative control group. When the treatment of the glycerol derivative compound of the present invention was added, it was confirmed that there are A73 and A75 derivatives that reduce cell migration similar to EC-18 (PLAG).

[Experimental Example 6] IL-4-Induced STAT6 Activity Reduction

In DMEM (Dulbecco Modified Eagle Medium, Hyclone, Thermo Scientific) medium to which 10% Fetal Bovine Serum was added, A549 cells were subcultured at a concentration of $1\times10^5$ cells/ml, and the cells were maintained in a 5% $CO_2$ humidified incubator at 37° C., and cultured. The cultured A549 cells were inoculated into a 48 well plate by $1\times10^5$ cells/ml and stabilized for 18 hours. Thereafter, pGL4-STAT6 reporter vector containing a STAT6 binding promoter portion was mixed with Attractene to induce complex formation at room temperature for 15 minutes. This complex was treated with the cells and then further incubated for 24 hours. Thereafter, the culture solution was treated with a glycerol derivative compounds of the type shown in Table 8 and Table 9 below for 1 hour in the culture solution, and then IL-4 (2 ng/ml or 10 ng/ml) was further incubated for 20 hours for STAT6 activity. Thereafter, the culture supernatant was removed for each well, and the remaining cells were lysed with a cell lysis buffer, and then cell lysate was recovered. 90 μl of luciferase reagent was mixed with 10 μl of the recovered cell lysate, and the degree of fluorescence was confirmed using a luminometer. The results are shown in Table 8 and Table 9 below.

TABLE 8

| | sample | Concentration (μg/ml) | STAT6 activity_ Luciferase activity (average ± deviation) |
|---|---|---|---|
| 1 | Negative control group | 0 | 8.5 ± 1.2 |
| 2 | IL-4 | 2 | 982.0 ± 38.7 |
| 3 | EC_18 | 100 | 462.5 ± 161.7 |
| 4 | EC-A04 | 100 | 1026 ± 275.9 |
| 5 | EC-A04-2 | 100 | 175.5 ± 28.2 |
| 6 | EC-A04_3 | 100 | 123.2 ± 11.5 |
| 7 | EC-A05 | 100 | 739.5 ± 197.6 |
| 8 | EC-A06 | 100 | 570.7 ± 52.9 |
| 9 | EC-A11 | 100 | 953 ± 98.9 |
| 10 | EC-A12 | 100 | 549.5 ± 96.5 |
| 11 | EC-A44 | 100 | 974.2 ± 37.4 |

TABLE 9

| | sample | Concentration (μg/ml) | STAT6 activity_ Luciferase activity (average ± deviation) |
|---|---|---|---|
| 1 | Negative control group | 0 | 12.5 ± 0.7 |
| 2 | IL-4 | 10 | 2134.5 ± 17.6 |
| 3 | EC_18 | 100 | 1281.5 ± 26.1 |
| 4 | EC_A59 | 100 | 1129 ± 5.6 |
| 5 | EC_A59A | 100 | 2127.5 ± 4.9 |
| 6 | EC_A60 | 100 | 2534.5 ± 40.3 |
| 7 | EC_60A | 100 | 1034.5 ± 12.0 |
| 8 | EC_A73 | 100 | 1176 ± 1.4 |
| 9 | EC_A73A | 100 | 625.5 ± 7.7 |
| 10 | EC_A74 | 100 | 2450 ± 16.9 |
| 11 | EC_A75 | 100 | 2308 ± 4.2 |
| 12 | EC_A76 | 100 | 1438 ± 7.0 |
| 13 | EC_A77 | 100 | 1819 ± 2.8 |
| 14 | EC_06A | 100 | 1552.5 ± 9.1 |

Figure 7:
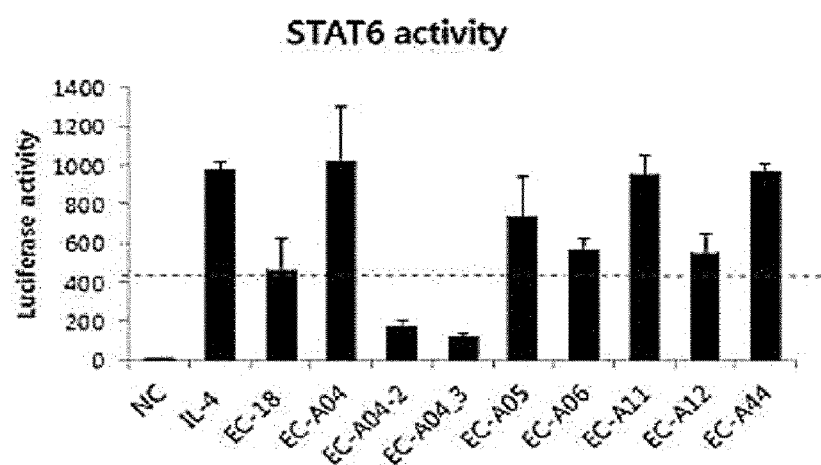
FIGS. 7 and 8 are graphs showing the degree of STAT6 activity induced by IL-4 according to another embodiment of the present invention.
Figure 8:
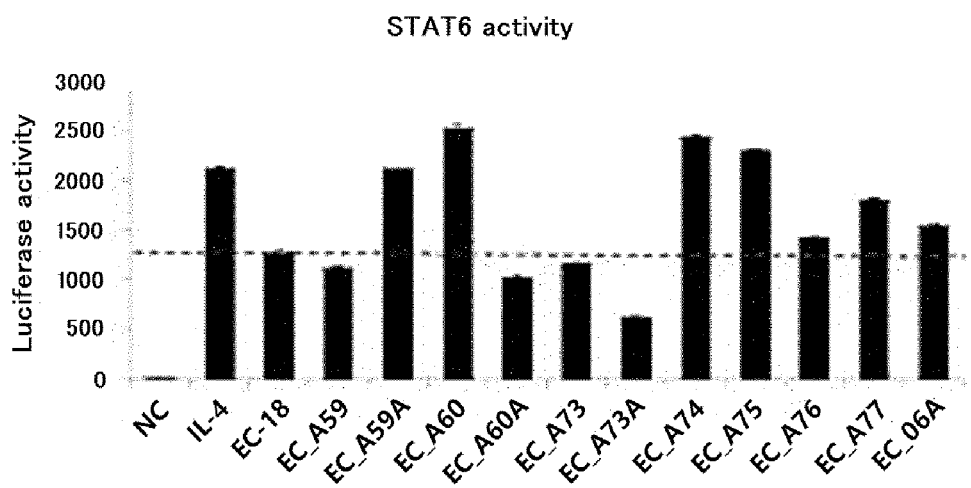

FIG. 7 and FIG. 8 are graphs which show the values in Table 8 and Table 9 above, which show the degree of STAT6 activity induced by the IL-4. As shown in Table 8, Table 9, FIG. 7 and FIG. 8, it were confirmed that when IL-4 was treated in A549 cells, the STAT6 activity was increased according to amount of the treated IL-4 by about 120 to 2000 times compared to the negative control group. When the EC-18 (PLAG) was treated, the STAT6 activity was reduced by about 50%. In the case of the glycerol derivative compound of the present invention, A04-2, A04-3, A06, A12, A59, A60A, A73, A73A and A76 are a derivative that significantly decreases STAT6 activity to a similar degree to EC-18 (PLAG), and it was confirmed that the STAT6 activity decreased to a degree similar to the results of most of the EC-18 treatment group. Among them, it was confirmed that A04-2, A04-3, and A73A significantly reduced STAT6 activity by up to about 80% compared to the EC-18 treatment group.

[Experimental Example 7] PKC Activator-Induced IL-4 Secretion Reduction

In DMEM (Dulbecco Modified Eagle Medium, Hyclone, Thermo Scientific) medium to which 10% Fetal Bovine Serum was added, EL-4 cells, a mouse lymphoma family, were subcultured at a concentration of $1 \times 10^5$ cells/ml, and the cells were maintained in a 5% $CO_2$ humidified incubator at 37° C., and cultured. The cultured EL-4 cells were inoculated into a 48 well plate by $5 \times 10^4$ cells/ml and stabilized for 30 hours. Then, the culture solution was treated with a glycerol derivative compounds of the type shown in Table 10 and Table 11 below for 2 hours. Thereafter, it were treated with 0.5 μg/ml of PKC activator (p10, some kind of PMA) of a cell stimulator, and subsequent further incubation were conducted for 18 hours. Thereafter 0.5 ml of the culture supernatant was collected for each well and centrifuged (at 3000 rpm, 5 minutes) to recover the supernatant. The IL-4 level in the recovered supernatant was measured according to the manual provided by the Mouse IL-4 ELISA set (BD Biosciences). The day before ELISA was carried out, the IL-4 capture antibody was diluted in phosphate buffered saline, coated on a microwell, and then stored at 4° C. overnight. Each well was washed three times with a buffer solution and then blocked with 2% Bovine Serum Albumin (BSA) for 1 hour at room temperature. After washing with a washing buffer solution three times, 100 μl of sample was dispensed into each well and left at room temperature for 2 hours. Detection antibody which was washed three times with a washing buffer solution and diluted was dispensed into each well and allowed to react at room temperature for 1 hour and left at room temperature for 1 hour. Thereafter, the secondary HRP conjugated antibody was reacted at room temperature for 30 minutes, washed three times with a washing buffer solution, and treated with 50 μl of stop solution for each well, and then the optical density was measured at 450 nm with an ELISA microplate leader. The results of the expression reduction rate were shown in Table 10 and Table 11 below.

TABLE 10

| | sample | Concentration (μg/ml) | IL-4 concentration (pg/μl, average ± deviation) |
|---|---|---|---|
| 1 | Negative control group | 0 | 1.5 ± 1.2 |
| 2 | PKC activator | 1 | 910.6 ± 25.7 |
| 3 | EC-18 | 100 | 662.4 ± 42.4 |
| 4 | EC_A59 | 100 | 1027.4 ± 22.4 |
| 5 | EC_A59A | 100 | 955.1 ± 26.9 |
| 6 | EC_A60 | 100 | 899.2 ± 61.0 |
| 7 | EC_60A | 100 | 774.7 ± 187.0 |
| 8 | EC_A73 | 100 | 1424.7 ± 210.2 |
| 9 | EC_A73A | 100 | 792 ± 220.4 |
| 10 | EC_A74 | 100 | 627 ± 3.8 |
| 11 | EC_A75 | 100 | 728.8 ± 23.1 |
| 12 | EC_A76 | 100 | 933.3 ± 140.1 |
| 13 | EC_A77 | 100 | 721.0 ± 89.3 |
| 14 | EC_A06A | 100 | 778.8 ± 86.1 |
| 15 | EC_A06 | 100 | 912.9 ± 10.9 |

TABLE 11

| | sample | Concentration (μg/ml) | IL-4 concentration (pg/μl, average ± deviation) |
|---|---|---|---|
| 1 | Negative control group | 0 | 0.6 ± 0.0 |
| 2 | PKC activator | 1 | 462.5 ± 57.1 |
| 3 | EC-18 | 100 | 189.8 ± 38.5 |
| 4 | EC_A104 | 100 | 183.2 ± 56.4 |
| 5 | EC_A105 | 100 | 154.7 ± 6.6 |
| 6 | EC_A106 | 100 | 166.9 ± 15.7 |
| 7 | EC_A107 | 100 | 175.0 ± 17.3 |
| 8 | EC_A111 | 100 | 165.6 ± 20.1 |
| 9 | EC_A112 | 100 | 171.6 ± 18.1 |
| 10 | EC_A113 | 100 | 198.5 ± 26.0 |
| 11 | EC_A114 | 100 | 277.8 ± 61.2 |

Figure 9:
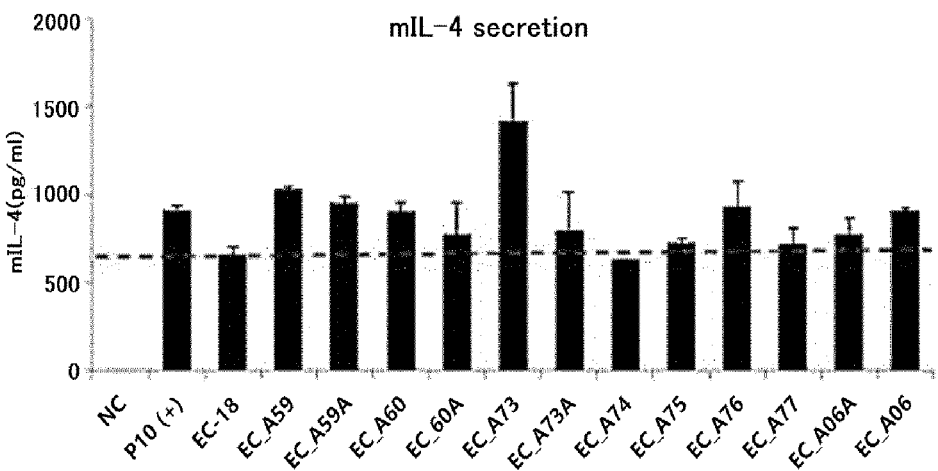
FIGS. 9 and 10 are graphs showing the degree of IL-4 secretion induced by PKC activator according to another embodiment of the present invention.
Figure 10:
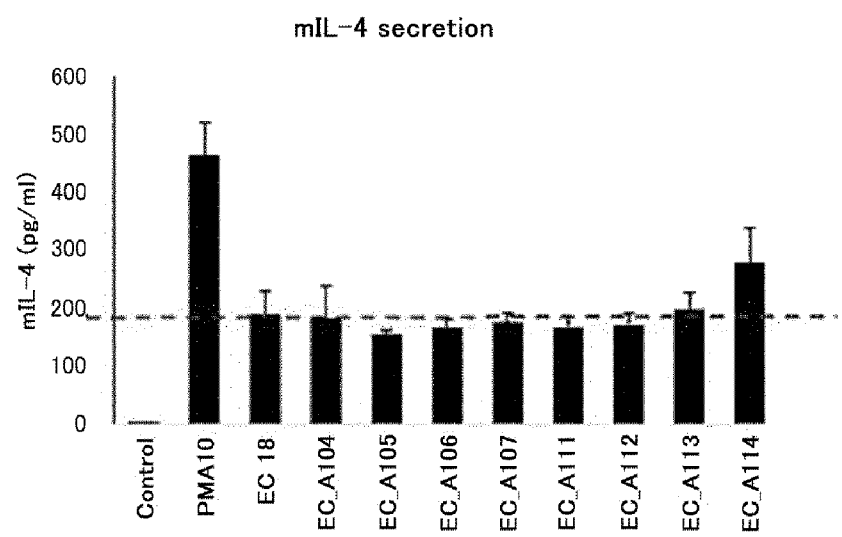

FIG. 9 and FIG. 10 are graphs which show the values in Table 8 and Table 9 above, which show the degree of IL-4 secretion induced by the PKC activator. As shown in Table 10, Table 11, FIG. 9 and FIG. 10, it were confirmed that when PKC activator were treated in mouse EL-4 cells, the secretion of IL-4 cytokine was rapidly increased by compared to the negative control group (Experiment 2). when EC-18 (PLAG) compound was treated, the IL-4 expression was decrease about 20% to 60% (Experiment 3). When the treatment of the glycerol derivative compound of the present invention is added, derivatives that reduce the secretion of IL-4 chemokine to a similar degree to EC-18 (PLAG) include A74, A75, A77, A104, A105, A106, A107, A111, A112 and A113. It was confirmed that the reduction was reduced from about 20% to 60%.

The invention claimed is:

1. A glycerol derivative represented by the following Chemical formula 3,

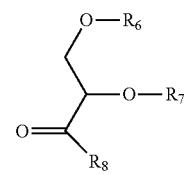

[Chemical formula 3]

in Chemical formula 3, $R_6$ and $R_7$ are independently palmitoyl or linoleoyl, and $R_8$ is $—OR_9$ or $—NHR_9$ (wherein, $R_9$ is ethyl).

2. A method for inhibiting or reducing an immune response by inhibiting overexpression of one or more inflammatory cytokines selected from the group consisting of IL-4, IL-6, and CXCL8 comprising a step of administering an effective amount of a glycerol derivative represented by the following Chemical formula 3 as an active ingredient to a subject in need thereof,

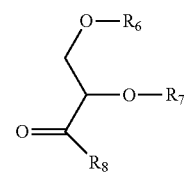

[Chemical formula 3]

in Chemical formula 3, $R_6$ and $R_7$ are independently a fatty acid group having 2 to 18 carbon atoms, and $R_8$ is $-OR_9$ or $-NHR_9$ (wherein, Ry is an alkyl group having 1 to 3 carbon atoms).

* * * * *